United States Patent
Zhu

(10) Patent No.: US 10,011,877 B2
(45) Date of Patent: Jul. 3, 2018

(54) TREATMENT OF BLADDER CANCER TO OVERCOME CHEMORESISTANCE

(71) Applicant: Genedia Biotech Co., Ltd., Kunshan, Jiangsu (CN)

(72) Inventor: Jingde Zhu, Jiangsu (CN)

(73) Assignee: GENEDIA BIOTECH CO., LTD., Yushan Town, Kunshan, Jiangsu (CN)

( * ) Notice: Subject to any disclaimer, the term of this patent is extended or adjusted under 35 U.S.C. 154(b) by 179 days.

(21) Appl. No.: 14/846,189

(22) Filed: Sep. 4, 2015

(65) Prior Publication Data

US 2017/0067113 A1    Mar. 9, 2017

(51) Int. Cl.
    *C12Q 1/6886*    (2018.01)

(52) U.S. Cl.
    CPC ..... *C12Q 1/6886* (2013.01); *C12Q 2600/106* (2013.01); *C12Q 2600/154* (2013.01); *C12Q 2600/158* (2013.01)

(58) Field of Classification Search
    None
    See application file for complete search history.

(56) References Cited

U.S. PATENT DOCUMENTS

2013/0310406 A1    11/2013    Jingde Zhu

OTHER PUBLICATIONS

Yafi et al., First- and second-line therapy for metastatic urothelial carcinoma of the bladder, 2011, Current Oncology, vol. 18, No. 1, pp. e25-e34.*

Lv et al., "The DNA methylation-regulated miR-193a-3p dictates the multi-chemoresistance of ladder cancer via repression of SRSF2/PLAU/HIC2 expression," Cell Death and Disease (2014), 195: 1-12.
Deng et al., "miR-193a-3p regulates the multi-drug resistance of bladder cancer by targeting the LOXL4 gene and the Oxidative Stress pathway ," Molecular Cancer (2014), 13:234: 1-13.
Lv et al., "MiR-193a-3p promotes the multi-chemoresistance of bladder cancer by targeting the HOXC9 gene," Cancer Letters (2014), 1-9.
Deng et al., "The miR-193a-3p regulated PSEN1 gene suppresses the multi-chemoresistance of bladder cancer," Biochimica et Biophysica Acta 1852 (2015), 520-528.
Li et al., "The miR-193a-3p regulated ING5 gene activates the DNA damage response pathway and inhibits multi-chemoresistance in bladder cancer," Oncotarget, vol. 6, No. 12 (2015), 10195-10206.
Ma et al., "DNA Methylation-regulated miR-193a-3p Dictates Resistance of Hepatocellular Carcinoma to 5-Fluorouracil via Repression of SFSF2 Expression," The Journal of Biological Chemistry, vol. 287, No. 8 (2012), 5639-5649.

* cited by examiner

*Primary Examiner* — Jeffrey S Lundgren
*Assistant Examiner* — Tori Strong
(74) *Attorney, Agent, or Firm* — Sheppard Mullin Richter & Hampton LLP

(57) ABSTRACT

The disclosure demonstrates the correlation of the methylation status of the miR-193a gene and the expression level of the miR-193a-3p transcript with the resistance of bladder cancer cells to certain chemotherapeutic drugs including pirarubicin (Pi), pacilitaxol (Pa), adriamycin (Ad), epirubicin hydrochloride (EH), and cispaltin (Ci), but not others (e.g, hydroxycamptothecin (Hy), gemcitabine (Ge) and mitomycin (Mi)). Further, the disclosure identifies seven target genes (SRSF2, PLAU, HIC2, LOXL4, HOXC9, PSEN1, and ING5) that are directly regulated by miR-193a-3p. The methylation/expression status of miR-193a-3p alone or in combination of the expression level of the target genes can serve as valuable indicators for chemotherapy outcome of a bladder cancer patient with a corresponding chemotherapeutic drug, and can be drug targets for sensitizing a bladder cancer patient for that drug.

6 Claims, 1 Drawing Sheet

TREATMENT OF BLADDER CANCER TO OVERCOME CHEMORESISTANCE

BACKGROUND

Bladder cancer (BCa) is the second most prevalent and the most deadly urogenital cancer in men. In addition to the high recurrence rates, BCa is refractory to chemotherapy and is thus considered one of the most difficult to treat. Although an eradication of primary lesions by chemotherapy is achievable in about half of the BCa patients, the cancer frequently recurs and becomes refractory to the second round of chemotherapy. Once chemoresistance is established, the cancer cells are resistant to multiple therapies, regardless of the type of the previous drug.

SUMMARY

It is discovered herein that the CpG island of the miR-193a gene is frequently methylated in bladder cancer cells that are sensitive to treatment of a variety of drugs (e.g., Pirarubicin (Pi), Pacilitaxel (Pa), Adriamycin (Ad), Epirubicin hydrochloride (EH), and Cispaltin(Ci)) and is not or lightly methylated in bladder cancer cells that are resistant to such chemotherapies. Such a correlation, however, does not exist for other drugs, such as Hydroxycamptothecin (Hy), Gemcitabine (Ge) and Mitomycin (Mi).

The miR-193a gene expresses two different mature microRNA, miR-193a-3p and miR-193a-5p. The methylation status of the miR-193a gene correlates with the expression level of the mature microRNA products. However, the examples show that that miR-193a-3p, not miR-193a-5p, impacts multi-drug resistant of bladder cancer cells.

The present examples further demonstrate that miR-193a-3p regulates drug resistance by directly targeting genes of various pathways, such as DNA damage, Notch, NF-κB, Myc/Max, and oxidative stress. Examples of the target genes include SRSF2, PLAU, HIC2, LOXL4, HOXC9, PSEN1, and ING5. Through manipulation of the expression of these genes and/or their protein products, it is further discovered that each of them, or various combinations thereof, contributes to chemoresistance of different drugs.

Interestingly, the combination of the miR-193a-3p status and expression level of each of the seven targeted genes exhibited further synergism in correlating to a bladder cancer cell's drug resistance. This is likely because each of the seven target genes is likely also regulated by other factors and makes unique contribution to the drug resistance of the lack thereof, and thus there is no one-to-one correlation between the status of miR-193a-3p and the expression level of the target genes.

These results are illustrated in FIGS. 1 and 2 and Tables 1 and 2 and is further summarized below in the chart. Accordingly, the status of miR-193a-3p alone, or together with that of each of the seven target genes is valuable in revealing a bladder cancer cell's sensitivity or resistance to a corresponding chemotherapeutic drug.

| Drug | Short Name | Correlation with miR-193a alone | Correlation with miR-193a-3p + |
|---|---|---|---|
| Pirarubicin | Pi | Yes | SRSF2, LOXL4, PSEN1, HOXC9 |
| Pacilitaxol | Pa | Yes | SRSF2, HIC2, PLAU, LOXL4, ING5 |
| Adriamycin | Ad | Yes | SRSF2, HIC2, PLAU, ING5 |
| Epirubicin hydrochloride | EH | Yes | SRSF2, LOXL4, ING5, HOXC9 |
| Cisplatin | Ci | Yes | LOXL4, ING5, PSEN1, HOXC9 |
| Hydroxycamptothecin | Hy | No | No |
| Gemcitabine | Ge | No | No |
| Mitomycin | Mi | No | No |

DETAILED DESCRIPTION OF THE DISCLOSURE

Figure 1:
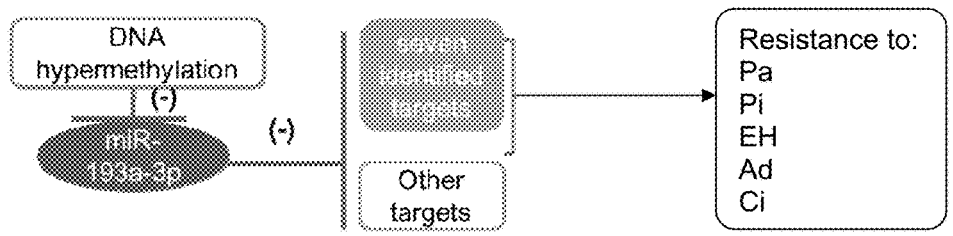
FIG. 1 illustrates the correlation between the methylation status of the miR-193a gene, the expression level of the miR-193a-3p RNA transcript, the expression level of the seven target genes, and a bladder cancer cell's resistance to any of the indicated chemotherapeutic drugs.

Throughout this disclosure, various publications, patents and published patent specifications are referenced by an identifying citation. The disclosures of these publications, patents and published patent specifications are hereby incorporated by reference into the present disclosure to more fully describe the state of the art to which this disclosure pertains.

Definitions

As used herein, certain terms may have the following defined meanings. As used in the specification and claims, the singular form "a," "an" and "the" include singular and plural references unless the context clearly dictates otherwise. For example, the term "a cell" includes a single cell as well as a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this disclosure. Accordingly, it is intended that the methods and compositions can include additional steps and components (comprising) or alternatively including steps and compositions of no significance (consisting essentially of) or alternatively, intending only the stated method steps or compositions (consisting of).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

The disclosure further provides diagnostic, prognostic and therapeutic methods, which are based, at least in part, on determination of the methylation status and/or expression level of a gene of interest identified herein.

For example, information obtained using the diagnostic assays described herein is useful for determining if a subject is suitable for cancer treatment of a given type (e.g., paclitaxel). Based on the prognostic information, a doctor can recommend a therapeutic protocol, useful for reducing the malignant mass or tumor in the patient or treat cancer in the individual.

Determining whether a subject is suitable or not suitable for cancer treatment of a given type, alternatively, can be expressed as identifying a subject suitable for the cancer treatment or identifying a subject not suitable for the cancer treatment of the given type.

It is to be understood that information obtained using the diagnostic assays described herein may be used alone or in combination with other information, such as, but not limited to, genotypes or expression levels of other genes, clinical chemical parameters, histopathological parameters, or age, gender and weight of the subject. When used alone, the information obtained using the diagnostic assays described herein is useful in determining or identifying the clinical outcome of a treatment, selecting a patient for a treatment, or treating a patient, etc.

When used in combination with other information, on the other hand, the information obtained using the diagnostic assays described herein is useful in aiding in the determination or identification of clinical outcome of a treatment, aiding in the selection of a patient for a treatment, or aiding in the treatment of a patient and etc. In a particular aspect, the genotypes or expression levels of one or more genes as disclosed herein are used in a panel of genes, each of which contributes to the final diagnosis, prognosis or treatment.

Diagnostic and Prognosis Methods

As described in the Summary above, it is discovered herein that the CpG island of the miR-193a gene is frequently methylated in bladder cancer cells that are sensitive to treatment of a variety of drugs (e.g., Pirarubicin (Pi), Paclitaxel (Pa), Adriamycin (Ad), Epirubicin hydrochloride (EH), and Cispaltin(Ci)) and not or lightly methylated in bladder cancer cells that are resistant to such chemotherapies. In addition, the disclosure had identified seven target genes (SRSF2, PLAU, HIC2, LOXL4, HOXC9, PSEN1, and ING5) that are directly targeted by miR-193a-3p. Accordingly, the methylation status of the miR-193a gene (or the directly correlated expression level of the miR-193a-3p transcript) alone with in combination with the expression level of the target genes serve as valuable indicators for revealing a bladder cancer cell's sensitivity or resistance to a corresponding chemotherapeutic drug.

"miR-193a" is microRNA gene. A representative sequence can be found at the GenBank with accession number NR_029710 (human). "miR-193a-3p" is a mature microRNA derived from the precursor microRNA miR-193a. A representative sequence of miR-193a-3p can be found at the microRNA database (mirdb.org) with Sanger accession No: MIMAT0000459: 5'-AACUGGCCUA-CAAAGUCCCAGU-3' (SEQ ID NO: 1, human, length=22).

Based on the instant discoveries, the methylation status of the miR-193a gene or the expression level of the miR-193a-3p RNA can be used to identify a bladder cancer patient suitable for certain chemotherapy. Such a method can further include checking the expression level of one or more of the seven target genes, for confirmation. Still, given the synergism between the status of miR-193a/miR-193-3p and the expression of the target genes, their combinations can serve as even stronger indicator or a bladder cancer patient's suitability to certain chemotherapy.

In one embodiment, provided is a method for determining whether or not a human bladder cancer patient is suitable for a therapy comprising the administration of a chemotherapeutic agent selected from the group consisting of pirarubicin, paclitaxel, adriamycin, epirubicin hydrochloride, and cisplatin. In some aspects, the method entails measuring, in a sample that comprises tumor DNA of the patient, the methylation status of one or more CpG sites associated with the miR-193a gene, and determining that the bladder cancer patient is suitable for the therapy if the CpG sites are methylated, or that the bladder cancer patient is not suitable for the therapy if the CpG sites are not methylated.

In some aspects, the sample is a urine sediment sample which includes tumor cells DNA or RNA of which can be extracted and analyzed In some aspects, the sample comprises a tumor cell, such as a biopsy or a surgical removed samples from the patient.

In some aspects, the method further comprises measuring the expression level of a target gene selected from SRSF2, PLAU, HIC2, LOXL4, HOXC9, PSEN1 and ING5 in the tumor cell, and determining that the bladder cancer patient is suitable for the therapy if the CpG sites are methylated and the expression level of the target gene is increased as compared to a control bladder cancer patient that is resistant to the therapy.

In another embodiment, provided is a method for identifying a suitable chemotherapeutic drug for a human bladder cancer patient, comprising measuring, in a sample that comprises a tumor cell of the patient, (a) the methylation status of one or more CpG sites associated with the miR-193a gene or the expression level of the miR-193a-3p RNA and (b) the expression level of a target gene selected from SRSF2, PLAU, HIC2, LOXL4, HOXC9, PSEN1 and ING5, and identifying the patient as suitable for therapy with:

(i) pirarubicin, if (a) the CpG sites are methylated or the expression level of the miR-193a-3p RNA is decreased as compared to a control bladder cancer patient that is resistant to pirarubicin and (b) the expression level of any one of SRSF2, LOXL4, PSEN1 and HOXC9 is increased as compared to a control bladder cancer patient that is resistant to pirarubicin;

(ii) paclitaxel, if (a) the CpG sites are methylated or the expression level of the miR-193a-3p RNA is decreased as compared to a control bladder cancer patient that is resistant to paclitaxel and (b) the expression level of any one of SRSF2, HIC2, PLAU, LOXL4 and ING5 is increased as compared to a control bladder cancer patient that is resistant to paclitaxel;

(iii) adriamycin, if (a) the CpG sites are methylated or the expression level of the miR-193a-3p RNA is decreased as compared to a control bladder cancer patient that is resistant to adriamycin and (b) the expression level of any one of SRSF2, HIC2, PLAU and ING5 is increased as compared to a control bladder cancer patient that is resistant to adriamycin;

(iv) epirubicin hydrochloride, if (a) the CpG sites are methylated or the expression level of the miR-193a-3p RNA is decreased as compared to a control bladder cancer patient that is resistant to epirubicin hydrochloride and (b) the expression level of any one of SRSF2, LOXL4, ING5 and HOXC9 is increased as compared to a control bladder cancer patient that is resistant to epirubicin hydrochloride; or (v) cisplatin, if (a) the CpG sites are methylated or the expression level of the miR-193a-3p RNA is decreased as compared to a control bladder cancer patient that is resistant to cisplatin and (b) the expression level of any one of LOXL4, ING5, PSEN1 and HOXC9 is increased as compared to a control bladder cancer patient that is resistant to cisplatin.

Determination of Increase or Decrease of an Expression Level or a Ratio

It would be readily appreciated by the skilled artisan that the increase or decrease of an expression level or a ratio are relative terms but can be readily ascertained.

In one aspect, an "internal control" can be used to normalize the measurement to correct sample collection variations. One such internal control is a "house keeping" gene that refers to any constitutively or globally expressed gene. Examples of such genes include, but are not limited to, β-actin, the transferring receptor gene, GAPDH gene or equivalents thereof. In one aspect of the disclosure, the internal control gene is β-actin. In one of aspect of the disclosure, the internal control gene for the miR-193a-3p is U6 RNA.

Normalized expression levels or ratios can then be compared to a suitable control sample. In one aspect, the control sample is a sample collected from a non-diseased (e.g., non-cancerous) subject or a non-diseased sample from the same subject.

In some such aspects, the term "overexpression" or "underexpression" refers to increased or decreased expression, or alternatively a differential expression, of a gene in a test sample as compared to the expression level of that gene in the control sample. In one aspect, the test sample is a diseased cell, and the control sample is a normal cell. In another aspect, the test sample is an experimentally manipulated or biologically altered cell, and the control sample is the cell prior to the experimental manipulation or biological alteration. In yet another aspect, the test sample is a sample from a patient, and the control sample is a similar sample from a healthy individual. In a yet further aspect, the test sample is a sample from a patient and the control sample is a similar sample from patient not having the desired clinical outcome. In one aspect, the differential expression is about 1.5 times, or alternatively, about 2.0 times, or alternatively, about 2.0 times, or alternatively, about 3.0 times, or alternatively, about 5 times, or alternatively, about 10 times, or alternatively about 50 times, or yet further alternatively more than about 100 times higher or lower than the expression level detected in the control sample. Alternatively, the gene is referred to as "over expressed" or "under expressed". Alternatively, the gene may also be referred to as "up regulated" or "down regulated".

In certain situations, no appropriate control samples can be identified, and the comparison is between two or more states of a sample, none of which is considered as a "norm". For instance, when neither "sensitive" nor "resistant" to a chemotherapy is considered the norm, the comparison can be made between each other or against a value that separates them.

In one scenario, the comparison is made between each other. For instance, it is observed that tumor cells resistant to a pirarubicin therapy generally have an expression level of Gene A that is about the same as the expression level of a housekeeping gene, GAPDH, and is rarely 2× or more higher than that. Meanwhile, it is observed that tumor cells sensitive to pirarubicin typically have much higher expression levels for Gene A. Accordingly, when the expression level of Gene A in a new test sample is measured as 10× as high as the expression level of GAPDH, it can be considered that the expression of Gene A in the new test sample is "increased," which thus indicates that the new test sample is likely sensitive to pirarubicin treatment.

In an alterative scenario, the increase or decrease can be compared to a "predetermined value" that separates two different states.

A "predetermined value" for a gene as used herein, is so chosen that a patient with an expression level of that gene higher than the predetermined value is likely to experience a more or less desirable clinical outcome than patients with expression levels of the same gene lower than the predetermined value, or vice-versa. Expression levels of genes, such as those disclosed in the present disclosure, are associated with clinical outcomes. One of skill in the art can determine a predetermined value for a gene by comparing expression levels of a gene in patients with more desirable clinical outcomes to those with less desirable clinical outcomes. In one aspect, a predetermined value is a gene expression value that best separates patients into a group with more desirable clinical outcomes and a group with less desirable clinical outcomes. Such a gene expression value can be mathematically or statistically determined with methods known in the art.

Using the same example as used above, if cells that are resistant to pirarubicin treatment generally have an expression level of 1× (times of GADPH expression level) of Gene A, and cells that are sensitive to pirarubicin treatment generally have an expression level of 5× (times of GADPH expression level), the predetermined value, for instance, can be set as 3× (times of GADPH expression level). Accordingly, an expression level of 1.5× (times of GADPH expression level) for Gene A in a new test sample would be considered "decreased", or lower than the predetermined value, which then indicates that the new test sample is likely resistant to pirarubicin treatment.

Predicable Clinical Outcomes

Clinical outcomes include, without limitation, response to therapy, overall survival or progression free survival, tumor recurrence, and adverse effects. Collectively, when a patient shows one or more positive clinical outcomes is sensitive to a therapy, the patient is considered "suitable" for the therapy, and therefore can be "selected" for the therapy.

"Response" to a therapy as used herein, generally refers a change of tumor mass in response to the therapy. More specifically, the terms "complete response," "partial response," "stable disease," "progressive disease," and "no response" are used to describe the level of tumor response.

A "complete response" (CR) to a therapy defines patients with evaluable but non-measurable disease, whose tumor and all evidence of disease had disappeared. A "partial response" (PR) to a therapy defines patients with anything less than complete response that were simply categorized as demonstrating partial response. "Stable disease" (SD) indicates that the patient is stable. "Progressive disease" (PD) indicates that the tumor has grown (i.e. become larger), spread (i.e. metastasized to another tissue or organ) or the overall cancer has gotten worse following treatment. For example, tumor growth of more than 20 percent since the start of treatment typically indicates progressive disease. "Disease free survival" indicates the length of time after treatment of a cancer or tumor during which a patient survives with no signs of the cancer or tumor. "Non-response" (NR) to a therapy defines patients whose tumor or evidence of disease has remained constant or has progressed.

The term "likely to respond" intends to mean that a patient is relatively more likely to experience a complete response or partial response than patients similarly situated without the methylation status or expression. Alternatively, the term "not likely to respond" intends to mean that the patient of a methylation status or expression is relatively less likely to experience a complete response or partial response than patients similarly situated without the genotype.

"Overall Survival" (OS) intends a prolongation in life expectancy as compared to naïve or untreated individuals or patients. Overall survival can be expressed as days, months or years of life span following the therapy.

"Progression free survival" (PFS) indicates the length of time during and after treatment that the cancer does not grow. Progression-free survival includes the amount of time patients have experienced a complete response or a partial response, as well as the amount of time patients have experienced stable disease.

"Tumor Recurrence" as used herein and as defined by the National Cancer Institute is cancer that has recurred (come back), usually after a period of time during which the cancer could not be detected. The cancer may come back to the same place as the original (primary) tumor or to another place in the body. It is also called recurrent cancer.

The term "suitable for a therapy" or "suitably treated with a therapy" shall mean that the patient is likely to exhibit one or more favorable clinical outcome as compared to a patient or patients having the same disease and receiving the same therapy but possessing a different characteristic that is under consideration for the purpose of the comparison. In one aspect, the characteristic under consideration is DNA methylation. In another aspect, the characteristic under consideration is expression level of a gene or a polypeptide. In one aspect, a more desirable clinical outcome is relatively higher likelihood of or relatively better tumor response such as tumor load reduction. In another aspect, a more desirable clinical outcome is relatively longer overall survival. In yet another aspect, a more desirable clinical outcome is relatively longer progression free survival or time to tumor progression. In yet another aspect, a more desirable clinical outcome is relatively longer disease free survival. In further another aspect, a more desirable clinical outcome is relative reduction or delay in tumor recurrence. In another aspect, a more desirable clinical outcome is relatively decreased metastasis. In another aspect, a more desirable clinical outcome is relatively lower relative risk. In yet another aspect, a more desirable clinical outcome is relatively reduced toxicity or side effects. In some embodiments, more than one clinical outcomes are considered simultaneously. In one such aspect, a patient possessing a characteristic may exhibit more than one more desirable clinical outcomes as compared to a patient to patients having the same disease and receiving the same therapy but not possessing the characteristic. As defined herein, the patient is considered suitable for the therapy. In another such aspect, a patient possessing a characteristic may exhibit one or more more desirable clinical outcome but simultaneously exhibit one or more less desirable clinical outcome. The clinical outcomes will then be considered collectively, and a decision as to whether the patient is suitable for the therapy will be made accordingly, taking into account the patient's specific situation and the relevance of the clinical outcomes. In some embodiments, disease free survival, progression free survival or overall survival is weighted more heavily than tumor response in a collective decision making.

Thus, one embodiment of the present disclosure provides a method for determining whether a human bladder cancer patient is suitable for a therapy comprising the administration of a chemotherapeutic agent selected from the group consisting of pirarubicin, pacilitaxel, adriamycin, epirubicin hydrochloride, and cisplatin. In some aspects, the method entails measuring, in a sample that comprises tumor DNA of the patient, the methylation status of one or more CpG sites associated with the miR-193a gene, and determining that the bladder cancer patient is suitable for the therapy if the CpG sites are methylated.

Another embodiment provides a method for aiding in the selection of or for selecting or not selecting a bladder cancer patient for a therapy comprising the administration of a chemotherapeutic agent selected from the group consisting of pirarubicin, pacilitaxel, adriamycin, epirubicin hydrochloride, and cisplatin, the method comprising measuring, in a sample that comprises tumor DNA of the patient, the methylation status of one or more CpG sites associated with the miR-193a gene, wherein the patient is selected for the therapy if the CpG sites are methylated.

Yet another embodiment of the disclosure provides a method for aiding in the determination of or for determining whether or not a bladder cancer patient is likely to respond to a therapy comprising the administration of a chemotherapeutic agent selected from the group consisting of pirarubicin, pacilitaxel, adriamycin, epirubicin hydrochloride, and cisplatin, the method comprising measuring, in a sample that comprises tumor DNA of the patient, the methylation status of one or more CpG sites associated with the miR-193a gene, wherein the presence of methylation of the CpG sites determines that the patient is likely to respond to the therapy, or the lack of methylation of the CpG sites determines that the patient is not likely respond to the therapy.

Such methods are also applicable to the combinations, as shown in Table 2.

It is noted that, even though the above embodiments use relative increase or decrease values to predict the clinical outcome, where the increase or decrease is as compared to a control patient that has the same cancer and is resistant to the therapy, the comparison can be alternatively made to appropriate predetermined values, as described above.

A "tumor sample" refers to any biological sample collected from a cancer patient that contains a tumor cell, a tumor DNA or RNA, or tumor protein or the like. It is appreciated that tumor cells can be collected from surgical resection or biopsy. As tumor cells can be leaked into the circulation system in a patient, tumor cells can be collected from blood or other circulation tissues. When a tumor cell breaks down, it can release certain DNA, RNA or protein that is characteristic of the tumor, such as methylated or mutated DNA that does not appear in normal cells. As such, a tumor sample does not necessarily include a tumor cell.

In another aspect, a tumor sample is any biological sample that contains substance or information, such as genetic polymorphisms, useful for revealing the status of a tumor. A "biological sample" as used herein includes, without limitation, a tissue or bodily fluid obtained from an animal, preferably a mammal and most preferably a human. For example, a biological sample can be urine sediments, biopsy material, bone marrow samples, blood, blood plasma, serum or cellular fraction thereof, urine, saliva, tears, or cells derived from a biological source. In one embodiment, the mammal is a human suspected of having or previously diagnosed as having or in need of screening for a cancer.

In some aspects, the tumor sample is collected for the measurement before the therapy is administered to the patient. In another aspect, the tumor sample is collected during the therapy, of after the therapy.

Methods of determining the methylation status of a DNA sequence is described above and further in the experimental examples. Methods of determining gene expression levels are known in the art. For the purpose of illustration only, such methods can include determining the amount of a mRNA transcribed from the gene using, for example, a method comprising, or alternatively consisting essentially of, or yet further consisting of, one or more of in situ hybridization, PCR, real-time PCR, or microarray. The methods can be performed on at least one of a fixed tissue, a frozen tissue, a biopsy tissue, a resection tissue, a micro-dissected tissue, or combinations thereof. Methods of determining protein expression levels are also known in the art, such as, without limitation, immunohistochemistry, ELISA or protein microarrays.

In addition, knowledge of the identity of the expression level of a gene in an individual (the gene profile) allows customization of therapy for a particular disease to the individual's genetic profile, the goal of "pharmacogenomics". For example, an individual's genetic profile can enable a doctor: 1) to more effectively prescribe a drug that will address the molecular basis of the disease or condition; 2) to better determine the appropriate dosage of a particular drug and 3) to identify novel targets for drug development. The identity of the genotype or expression patterns of individual patients can then be compared to the genotype or expression profile of the disease to determine the appropriate drug and dose to administer to the patient.

The ability to target populations expected to show the highest clinical benefit, based on the normal or disease genetic profile, can enable: 1) the repositioning of marketed drugs with disappointing market results; 2) the rescue of drug candidates whose clinical development has been discontinued as a result of safety or efficacy limitations, which are patient subgroup-specific; and 3) an accelerated and less costly development for drug candidates and more optimal drug labeling.

The methods described herein may be performed, for example, by utilizing pre-packaged diagnostic kits, such as those described below, comprising at least one probe or primer nucleic acid described herein, which may be conveniently used, e.g., to determine whether a subject is likely to experience tumor recurrence following therapy as described herein or has or is at risk of developing disease such as colon cancer.

Diagnostic procedures can also be performed in situ directly upon tissue sections (fixed and/or frozen) of primary tissue such as biopsies obtained from biopsies or resections, such that no nucleic acid purification is necessary. Nucleic acid reagents can be used as probes and/or primers for such in situ procedures (see, for example, Nuovo, G. J. (1992) PCR IN SITU HYBRIDIZATION: PROTOCOLS AND APPLICATIONS, RAVEN PRESS, NY).

In addition to methods which focus primarily on the detection of one nucleic acid sequence, profiles can also be assessed in such detection schemes. Fingerprint profiles can be generated, for example, by utilizing a differential display procedure, Northern analysis and/or RT-PCR.

Methods and Compositions of Treatment

This disclosure also provides a method for treating a cancer patient selected for therapy based on the presence of a genetic characteristics as described above, comprising administering an effective amount of a therapy to the patient, wherein the patient is identified by a method described above as suitable for the therapy, thereby treating the patient. For those determined to be likely not suitable for the therapy, alternative treatment methods can be used.

The term "treating" as used herein is intended to encompass curing as well as ameliorating at least one symptom of the condition or disease. For example, in the case of cancer, a response to treatment includes a reduction in tumor mass, increase in survival time, elongation in time to tumor progression, reduction in tumor mass, reduction in tumor burden and/or a prolongation in time to tumor metastasis, time to tumor recurrence, tumor response, complete response, partial response, stable disease, progressive disease, progression free survival, overall survival, each as measured by standards set by the National Cancer Institute and the U.S. Food and Drug Administration for the approval of new drugs. See Johnson et al. (2003) J. Clin. Oncol. 21(7):1404-1411.

"A therapeutically effective amount" or "an effective amount" intends to indicate the amount of a compound or agent administered or delivered to the patient which is most likely to result in the desired response to treatment. The amount is empirically determined by the patient's clinical parameters including, but not limited to the stage of disease, age, gender, histology, sensitivity, toxicity and likelihood for tumor recurrence.

Treatment of Patients Selected as Suitable for the Therapy

In one aspect, the patient is determined to be able to exhibit positive clinical outcomes for a treatment, based on the examination of the methylation status of the miR-193a gene, the expression level of miR-193a-3p or any of SRSF2, PLAU, HIC2, LOXL4, HOXC9, PSEN1 and ING5.

Accordingly, one embodiment of the present disclosure provides a method for treating a bladder cancer patient, comprising administering to the patient an effective amount of a therapy identified as suitable to the patient.

In one aspect, the patient has methylation of one or more of the CpG sites associated with miR-193a or increased expression of the miR-193a-3p RNA in a tumor cell, and thus is treated with any one or more of pirarubicin, pacilitaxel, adriamycin, epirubicin hydrochloride, and cisplatin. In some aspect, the patient further has increased expression of any of the SRSF2, PLAU, HIC2, LOXL4, HOXC9, PSEN1 and ING5 genes.

In one aspect, the suitable therapy is identified as (i) pirarubicin, if (a) the CpG sites are methylated or the expression level of the miR-193a-3p RNA is decreased as compared to a control bladder cancer patient that is resistant to pirarubicin and (b) the expression level of any one of SRSF2, LOXL4, PSEN1 and HOXC9 is increased as compared to a control bladder cancer patient that is resistant to pirarubicin;

(ii) pacilitaxel, if (a) the CpG sites are methylated or the expression level of the miR-193a-3p RNA is decreased as compared to a control bladder cancer patient that is resistant to pacilitaxel and (b) the expression level of any one of SRSF2, HIC2, PLAU, LOXL4 and ING5 is increased as compared to a control bladder cancer patient that is resistant to pacilitaxel;

(iii) adriamycin, if (a) the CpG sites are methylated or the expression level of the miR-193a-3p RNA is decreased as compared to a control bladder cancer patient that is resistant to adriamycin and (b) the expression level of any one of SRSF2, HIC2, PLAU and ING5 is increased as compared to a control bladder cancer patient that is resistant to adriamycin;

(iv) epirubicin hydrochloride, if (a) the CpG sites are methylated or the expression level of the miR-193a-3p RNA is decreased as compared to a control bladder cancer patient that is resistant to epirubicin hydrochloride and (b) the expression level of any one of SRSF2, LOXL4, ING5 and HOXC9 is increased as compared to a control bladder cancer patient that is resistant to epirubicin hydrochloride; or (v) cisplatin, if (a) the CpG sites are methylated or the expression level of the miR-193a-3p RNA is decreased as compared to a control bladder cancer patient that is resistant to cisplatin and (b) the expression level of any one of LOXL4, ING5, PSEN1 and HOXC9 is increased as compared to a control bladder cancer patient that is resistant to cisplatin. The identified suitable therapy is then administered to the patient, accordingly.

In one aspect, the therapy further comprises radiation therapy.

Treatment of Patients Determined to Exhibit Unfavorable Clinical Outcomes from a Therapy It is contemplated that some patients would exhibit genetic characteristics indicative of unfavorable clinical outcomes if treated with a drug (a "primary therapy") because the tumor cells may not be sensitive enough to the treatment. For such patients, a co-administration of an agent (the "sensitizing agent") that inhibits the miR-193a gene or activates any of the seven target genes so as to render the tumor sensitive to the therapy is appropriate.

In some aspects, the sensitizing agent is administered concurrently with the primary therapy. In other aspects, the sensitizing agent is administered prior to or following the administration of the primary therapy. When the sensitizing agent is administered prior to the administration of the primary therapy, the sensitizing agent can be administered at least about 1 hour, 2 hours, 4 hours, 6 hours, 12 hours, 1 day, 2 days, 3 days, 4 days, 5 days, or 6 days prior to the administration of the primary therapy.

The sensitizing agents can be readily prepared and examples are provided in the experimental example, such as miR-193a-3p antagomir.

Inhibiting or enhancing the "biological activity" of a gene, a protein, or an RNA, as used herein, includes without limitation inhibiting or enhancing the expression, the protein or RNA activity, the proper localization or modification of the gene, protein, or RNA molecules.

Generally, such agents include one type that activates the activity or expression of a gene or gene product (e.g., SRSF2, PLAU, HIC2, LOXL4, HOXC9, PSEN1 and ING5) and another type that represses the activity or expression of a gene or gene product (e.g., miR-193a-3p, SRSF2, PLAU, HIC2, LOXL4, HOXC9, PSEN1 and ING5). Methods of designing and preparing both types of agents are well known in the art and briefly described below. Moreover, an agent that specifically induces methylation of a gene can also be readily prepared with known methods.

Non-limiting examples of such agents include a miR-193-3p antagomir, a nucleic acid that encloses one or more of the target genes, or a protein product of the target genes.

Methods for Inducing Methylation of a Gene in a Cell

Methods of site-specific changing the DNA methyaltion state, e.g., the methylation status at certain CpG site of the miR-193a gene, are known in the art. For instance, Xu and Bestor (Xu et al. (1997) *Nat Genet,* 17, 376-378) describe a method to specifically induce CpG methylation targeted at a predetermined sequence. As the genomic sequence of the miR-193a gene is known and the CpG sites, which when methylated can suppress the expression of the miR-193a-3p RNA, have been disclosed and examined in the present experimental example, Xu and Bestor's method can readily adopted to induce, in vitro or in vivo, methylation of these CpG sites leading to decreased expression of the miR-193a-3p RNA.

Methods for Decreasing the Biological Activity of a Gene in a Cell

An agent that decreases the biological activity of a gene, such as miR-193a-3p can be a antagomir, or a siRNA, a ribozyme, without limitation.

Antagomirs are a class of chemically engineered oligonucleotides and can be used to silence endogenous microRNA. An antagomir is a small synthetic RNA that is perfectly complementary to the specific miRNA target with either mispairing at the cleavage site of Ago2 or some sort of base modification to inhibit Ago2 cleavage. Usually, antagomirs have some sort of modification, such as 2' methoxi groups and phosphothioates, to make it more resistant to degradation. Methods of designing and using antagomirs are known in the art, see, Krützfeldt et al., (2005). *Nature* 438 (7068): 685-9.

Methods for Increasing the Activity or Expression of a Gene in a Cell

Methods for increasing the level of a protein, or polypeptide or peptide, such as SRSF2, in a cell are known in the art. In one aspect, the SRSF2 level is increased by increasing the amount of a polynucleotide encoding SRSF2, as provided above, wherein that polynucleotide is expressed such that new SRSF2 is produced. In another aspect, increasing the SRSF2 level is increased by increasing the transcription of a polynucleotide encoding SRSF2, or alternatively translation of SRSF2, or alternatively post-translational modification, activation or appropriate folding of SRSF2. In yet another aspect, increasing SRSF2 level is increased by increasing the binding of the protein to appropriate cofactor, receptor, activator, ligand, or any molecule that is involved in the protein's biological functioning. In some embodiments, increasing the binding of SRSF2 to the appropriate molecule is increasing the amount of the molecule. In one aspect of the embodiments, the molecule is the SRSF2 protein. In another aspect of the embodiments, the molecule is a small molecule. In a further aspect of the embodiments, the molecule is a polynucleotide.

Methods of increasing the amount of polynucleotide in a cell are known in the art and can be modified for increasing the amount of a polynucleotide encoding SRSF2. In one aspect, the polynucleotide can be introduced to the cell and expressed by a gene delivery vehicle that can include a suitable expression vector.

Suitable expression vectors are well-known in the art, and include vectors capable of expressing a polynucleotide operatively linked to a regulatory element, such as a promoter region and/or an enhancer that is capable of regulating expression of such DNA. Thus, an expression vector refers to a recombinant DNA or RNA construct, such as a plasmid, a phage, recombinant virus or other vector that, upon introduction into an appropriate host cell, results in expression of the inserted DNA. Appropriate expression vectors include those that are replicable in eukaryotic cells and/or prokaryotic cells and those that remain episomal or those which integrate into the host cell genome.

As used herein, the term "vector" refers to a non-chromosomal nucleic acid comprising an intact replicon such that the vector may be replicated when placed within a cell, for example by a process of transformation. Vectors may be viral or non-viral. Viral vectors include retroviruses, adenoviruses, herpesvirus, papovirus, or otherwise modified naturally occurring viruses. Exemplary non-viral vectors for delivering nucleic acid include naked DNA; DNA complexed with cationic lipids, alone or in combination with cationic polymers; anionic and cationic liposomes; DNA-protein complexes and particles comprising DNA condensed with cationic polymers such as heterogeneous polylysine, defined-length oligopeptides, and polyethylene imine, in some cases contained in liposomes; and the use of ternary complexes comprising a virus and polylysine-DNA.

Non-viral vector may include plasmid that comprises a heterologous polynucleotide capable of being delivered to a target cell, either in vitro, in vivo or ex-vivo. The heterologous polynucleotide can comprise a sequence of interest and can be operably linked to one or more regulatory elements and may control the transcription of the nucleic acid sequence of interest. As used herein, a vector need not be capable of replication in the ultimate target cell or subject. The term vector may include expression vector and cloning vector.

Gene delivery vehicles also include DNA/liposome complexes, micelles and targeted viral protein-DNA complexes. Liposomes that also comprise a targeting antibody or fragment thereof can be used in the methods of this invention. To enhance delivery to a cell, the nucleic acid or proteins of this invention can be conjugated to antibodies or binding fragments thereof which bind cell surface antigens, e.g., a cell surface marker found on stem cells or cardiomyocytes. In addition to the delivery of polynucleotides to a cell or cell population, direct introduction of the proteins described herein to the cell or cell population can be done by the non-limiting technique of protein transfection, alternatively culturing conditions that can enhance the expression and/or promote the activity of the proteins of this invention are other non-limiting techniques.

Proteins have been described that have the ability to translocate desired nucleic acids across a cell membrane. Typically, such proteins have amphiphilic or hydrophobic subsequences that have the ability to act as membrane-translocating carriers. For example, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz (1996) Current Opinion in Neurobiology 6:629-634. Another subsequence, the h (hydrophobic) domain of signal peptides, was found to have similar cell membrane translocation characteristics (see, e.g., Lin et al. (1995) J. Biol. Chem. 270:14255-14258). Such subsequences can be used to translocate oligonucleotides across a cell membrane. Oligonucleotides can be conveniently derivatized with such sequences. For example, a linker can be used to link the oligonucleotides and the translocation sequence. Any suitable linker can be used, e.g., a peptide linker or any other suitable chemical linker.

Methods of delivering a protein to a cell, either to increase the biological activity of itself or a protein positively regulated by this protein, or to decrease the biological activity of a protein negatively regulated by this protein, are generally known in the art. For example, SRSF2 can be delivered to a eukaryotic cell by a type III sercreation machine. See, e.g., Galan and Wolf-Watz (2006) Nature 444:567-73. Biologically active and full length protein, for another example, can also be delivered into a cell using cell penetraint peptides (CPP) as delivery vehicles. The trans-activating transcriptional activator (TAT) from human immunodeficiency virus 1 (HIV-1) is such a CPP, which is able to deliver different proteins, such as horseradish peroxidase and RNase A across cell membrane into the cytoplasm in different cell lines. Wadia et al. (2004) Nat. Med 10:310-15. Accordingly, in one aspect, SRSF2 can be delivered to a cell using TAT as a vehicle to increase the biological activity of SRSF2 in the cell.

Liposomes, microparticles and nanoparticles are also known to be able to facilitate delivery of proteins or peptides to a cell by encapsulating the peptides (reviewed in Tan et al. (2010) Peptides 31(1):184-93). The liposomes, microparticles or nanoparticles can also comprise a targeting antibody or fragment thereof can be used in the methods of this invention. To enhance delivery to a cell, the proteins can be conjugated to antibodies or binding fragments thereof which bind cell surface antigens, e.g., a cell surface marker found on progentior cells.

In another aspect, non-covalent method which forms CPP/protein complexes has also been developed to address the limitations in covalent method such as chemical modification before crosslinking and denaturation of proteins before delivery. For example, a short amphipathic peptide carrier, Pep-1 and protein complexes have proven effective for delivery. It was shown that Pep-1 could facilitate rapid cellular uptake of various peptides, proteins and even full-length antibodies with high efficiency and less toxicity. Cheng et al. (2001) Nat. Biotechnol. 19:1173-6.

The therapies can be administered by any suitable formulation. Accordingly, a formulation comprising the necessary therapy is further provided herein. The formulation can further comprise one or more preservatives or stabilizers. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4., 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3. 0.4, 0.5, 0.9, 1.0%), 0.1-3% benzyl alcohol (e.g., 0.5, 0.9, 1.1., 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, and 1.0%).

The chemotherapeutic agents or drugs can be administered as a composition. A "composition" typically intends a combination of the active agent and another carrier, e.g., compound or composition, inert (for example, a detectable agent or label) or active, such as an adjuvant, diluent, binder, stabilizer, buffers, salts, lipophilic solvents, preservative, adjuvant or the like and include pharmaceutically acceptable carriers. Carriers also include pharmaceutical excipients and additives proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this disclosure, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

The term carrier further includes a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Additional carriers include polymeric excipients/additives such as polyvinylpyrrolidones, ficolls (a polymeric sugar), dextrates (e.g., cyclodextrins, such as 2-hydroxypropyl-.quadrature.-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives and any of the above noted carriers with the additional proviso that they be acceptable for use in vivo. For examples of carriers, stabilizers and adjuvants, see Martin REMINGTON'S PHARM. SCI., 15th Ed. (Mack Publ. Co., Easton (1975) and Williams & Williams, (1995), and in the "PHYSICIAN'S DESK REFERENCE", 52$^{nd}$ ed., Medical Economics, Montvale, N.J. (1998).

Many combination chemotherapeutic regimens are known to the art, such as combinations of platinum compounds and taxanes, e.g. carboplatin/paclitaxel, capecitabine/docetaxel, the "Cooper regimen", fluorouracil-levamisole, fluorouracil-leucovorin, fluorouracil/oxaliplatin, methotrexate-leucovorin, and the like.

Combinations of chemotherapies and molecular targeted therapies, biologic therapies, and radiation therapies are also well known to the art; including therapies such as trastuzumab plus paclitaxel, alone or in further combination with platinum compounds such as oxaliplatin, for certain breast cancers, and many other such regimens for other cancers; and the "Dublin regimen" 5-FU IV over 16 hours on days 1-5 and 75 mg/m$^2$ cisplatin IV or oxaliplatin over 8 hours on day 7, with repetition at 6 weeks, in combination with 40 Gy radiotherapy in 15 fractions over the first 3 weeks) and the "Michigan regimen" (fluorouracil plus cisplatin or oxaliplatin plus vinblastine plus radiotherapy), both for esophageal cancer, and many other such regimens for other cancers, including colorectal cancer.

In another aspect of the disclosure, the method for treating a patient further comprises, or alternatively consists essentially of, or yet further consists of surgical resection of a metastatic or non-metastatic solid malignant tumor and, in some aspects, in combination with radiation. Methods for treating these tumors as Stage I, Stage II, Stage III, or Stage IV by surgical resection and/or radiation are known to one skilled in the art. Guidelines describing methods for treatment by surgical resection and/or radiation can be found at the National Comprehensive Cancer Network's web site, nccn.org, last accessed on May 27, 2008.

The disclosure provides an article of manufacture, comprising packaging material and at least one vial comprising a solution of the chemotherapy as described herein and/or or at least one antibody or its biological equivalent with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The disclosure further comprises an article of manufacture, comprising packaging material, a first vial comprising the chemotherapy and/or at least one lyophilized antibody or its biological equivalent and a second vial comprising an aqueous diluent of prescribed buffer or preservative, wherein said packaging material comprises a label that instructs a patient to reconstitute the therapeutic in the aqueous diluent to form a solution that can be held over a period of twenty-four hours or greater.

Chemotherapeutic formulations of the present disclosure can be prepared by a process which comprises mixing at least one antibody or biological equivalent and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing of the antibody and preservative in an aqueous diluent is carried out using conventional dissolution and mixing procedures. For example, a measured amount of at least one antibody in buffered solution is combined with the desired preservative in a buffered solution in quantities sufficient to provide the antibody and preservative at the desired concentrations. Variations of this process would be recognized by one of skill in the art, e.g., the order the components are added, whether additional additives are used, the temperature and pH at which the formulation is prepared, are all factors that can be optimized for the concentration and means of administration used.

The compositions and formulations can be provided to patients as clear solutions or as dual vials comprising a vial of lyophilized antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available. Recognized devices comprising these single vial systems include those pen-injector devices for delivery of a solution such as BD Pens, BD Autojectore, Humaject® NovoPen®, B-D®Pen, AutoPen®, and OptiPen®, GenotropinPen®, Genotronorm Pen®, Humatro Pen®, Reco-Pen®, Roferon Pen®, Biojector®, iject®, J-tip Needle-Free Injector®, Intraject®, Medi-Ject®, e.g., as made or developed by Becton Dickensen (Franklin Lakes, N.J. available at bectondickenson.com), Disetronic (Burgdorf, Switzerland, available at disetronic.com; Bioject, Portland, Oreg. (available at bioject.com); National Medical Products, Weston Medical (Peterborough, UK, available at weston-medical.com), Medi-Ject Corp (Minneapolis, Minn., available at mediject.com).

Various delivery systems are known and can be used to administer a chemotherapeutic agent of the disclosure, e.g., encapsulation in liposomes, microparticles, microcapsules, expression by recombinant cells, receptor-mediated endocytosis. See e.g., Wu and Wu (1987) J. Biol. Chem. 262: 4429-4432 for construction of a therapeutic nucleic acid as part of a retroviral or other vector, etc. Methods of delivery include but are not limited to intra-arterial, intra-muscular, intravenous, intranasal and oral routes. In a specific embodiment, it may be desirable to administer the pharmaceutical compositions of the disclosure locally to the area in need of treatment; this may be achieved by, for example, and not by way of limitation, local infusion during surgery, by injection or by means of a catheter.

The agents identified herein as effective for their intended purpose can be administered to subjects or individuals identified by the methods herein as suitable for the therapy. Therapeutic amounts can be empirically determined and will vary with the pathology being treated, the subject being treated and the efficacy and toxicity of the agent.

Also provided is a therapy or a medicament comprising an effective amount of a chemotherapeutic as described herein for treatment of a human cancer patient having the appropriate expression level of the gene of interest as identified in the experimental examples. Further provided is a therapy comprising a platinum drug, or alternatively a platinum drug therapy, for use in treating a human cancer patient having the appropriate expression level of the gene of interest as identified in the experimental examples.

Methods of administering pharmaceutical compositions are well known to those of ordinary skill in the art and include, but are not limited to, oral, microinjection, intravenous or parenteral administration. The compositions are intended for topical, oral, or local administration as well as intravenously, subcutaneously, or intramuscularly. Administration can be effected continuously or intermittently throughout the course of the treatment. Methods of determining the most effective means and dosage of administration are well known to those of skill in the art and will vary with the cancer being treated and the patient and the subject being treated. Single or multiple administrations can be carried out with the dose level and pattern being selected by the treating physician.

EXPERIMENTAL DETAILS

Example 1. DNA Methylation-Regulated miR-193a-3p Dictates the Multi-Chemoresistance of Bladder Cancer Via Repression of SRSF2/PLAU/HIC2 Expression Chemoresistance hinders the curative cancer chemotherapy. To define the role of the DNA methylation-regulated microRNA (miR) genes in the chemoresistance of bladder cancer, this example performed both DNA methylomic and miRomic analyses of a multi-chemo-sensitive (5637) versus a multi-chemoresistant (H-bc) cell line and found that miR-193a-3p was hypermethylated/silenced in the 5637 cells and hypomethylated/expressed in the H-bc cells. Forced reversal of its level turned around the chemoresistance in the cultured cells and the tumor xenografts in nude mice. Three of the target genes of miR-193a-3p, SRSF2, PLAU and HIC2, worked in concert to relay the miR-193a-3p's impact on the bladder cancer chemoresistance by modulating the activities of the following five signaling pathways: DNA damage, Notch, NF-κB, Myc/Max, and Oxidative Stress. In addition to the mechanistic insights in how the newly identified miR-193a-3p/SRSF2, PLAU, HIC2/five signaling pathway axis regulates the chemoresistance of bladder cancer cells, this study provides a new set of diagnostic targets for the guided personalized chemotherapy of bladder cancer. More details of this example can be found in Lv et al., "THE DNA METHYLATION-REGULATED MIR-193A-3P DICTATES THE MULTI-CHEMORESISTANCE OF BLADDER CANCER VIA REPRESSION OF SRSF2/PLAU/HIC2 EXPRESSION," Cell Death Dis. 5:e1402 (2014), the content of which is incorporated to the present disclosure by reference.

Materials and Methods

Studies in Cell Culture

Cell lines: Five transitional carcinoma cell lines of BCa used in this study: EJ (established by Marshall CJ in 1977), T24 (ATCC NO. HTB-4), 5637 (ATCC NO. HTB-9), H-bc (established by cancer research Institute of Kunming Medical College, 1986), and Biu87 (established by department of Urology of Beijing Medical University in 1987) were purchased from the Chinese Academy of Sciences Committee on Culture Collection Cell Bank, Shanghai Institutes for Biological Sciences, Shanghai, China. Cells are cultured in RPMI1640 (Invitrogen, Carlsbad, Calif., USA)+10% fetal bovine serum (Invitrogen) and 1% glutamine at 37° C. in 5% $CO_2$.

The mimic/antagomiR/siRNA/overexpression plasmids transfection: all the mimic, antagomiR, siRNA, and the scramble sequence control (NC) as well as riboFECT CP transfection kit were supplied by Guangzhou Ribobio (Guangzhou, China). The mammalian expression constructs for PLAU (EX-F0073-M98-5) and SRSF2 (EX-F0622-M98-5) with GFP tag were supplied by Guangzhou Fulengen (Guangzhou, China). Transfection of both ribonucleic acid reagents or plasmids mentioned above and the reporter plasmids in a Cignal Finder Pathway Reporter package (Qiagen, Hilden, Germany) was performed according to the manufacturer's instruction.

The Luciferase Reporter Assay

A full length of the human PLAU 3'-untranslated region (932 bp) and partial length of HIC2 3'-UTR (1131 bp, 1862-2992 from a 4719-bp full length) with the miR-193a-3p targeting sequence were cloned at the downstream of the firefly luciferase gene in pGL3 (Invitrogen) to construct pGL3-luc-PLAU and pGL3-luc-HIC2, respectively. All the constructs were confirmed by restriction digestion.

Cells were seeded into 96-well plates at around $1 \times 10^4$ cells per well and transfected with a mixture of 50 ng pGL3-luc-PLAU or pGL3-luc-HIC2, 5 ng Renilla plus 5 pmol mimic or scramble control (NC) nucleotides, with the riboFECT CP transfection reagents according to the manufacturer's instruction. Both firefly and Renilla luciferase activities were measured 18 h after transfection by the Dual-Luciferase Reporter Assay System (Promega) using a Promega GloMax 20/20 luminometer. The relative firefly luciferase activities were normalized with the *Renilla* luciferase activities as a for transfection efficiency.

The pathway luciferase reporter constructs: (1) the negative control construct: the firefly luciferase gene is under the control of the minimal promoter. (2) the pathway reporter construct: a tandem repeat of the cognate consensus motif that is recognized by each master transcription factor for the corresponding pathway was placed at the upstream of the minimal promoter in the construct 1. (3) the positive control construct: the firefly luciferase gene is under the control of CMV promoter and (4) the internal control construct. The firefly luciferase gene in construct 3 was replaced with the *Renilla* luciferase gene. The analysis was carried out according to the manufacturer's instruction (Qiagen). Briefly, the cells were transfected in triplet with each firefly luciferase reporter construct in combination with the *Renilla* luciferase construct using ribo FECT CP transfection reagent, and both luciferase activities in cell extracts at 24 h after transfection were measured by a Promega Dual-Luciferase Reporter assay (Promega) using a Promega GloMax 20/20 luminometer. Firefly luciferase activities from each set were normalized to the activity of *Renilla* luciferase to control the inter-transfection bias. The relative luciferase activities (luciferase unit) of the pathway reporter over the negative control in the transfected cells were calculated as a measurement of the pathway activity.

Chemotherapeutics: All the chemotherapeutic drugs used are of the clinic grade (NCI Dictionary of Cancer Terms), Pi: Pirarubicin hydrochloride (Wanle, Shenzhen, China); Pa: Paclitaxel (Shuanglu, Beijing, China); Ad: Adriamycin (Haizheng, Zhejiang, China); EH: Epirubicin hydrochloride (Haizheng, Zhejiang, China).

Chemoresistance profiling ($IC_{50}$ measurements): Cells in the logarithmic phase of growth were seeded in triplicate in 96-well plates at the density of $0.5 \times 10^4$/well and treated with four-fold serially diluted drugs for 72 h. Cell survival was then measured by a thiazolyl blue tetrazolium bromide (MTT, 490 nm reading)-based cell proliferation assay. Both the linear regression parameters and the $IC_{50}$ (the concentration of drug required for 50% of cells to be killed) with the no-drug control as the reference were calculated. The relative chemoresistance was presented as the fold for each of the cell line over the lowest $IC_{50}$.

RNA Analysis

Total RNA was isolated using the TRIzol reagent (Tiangen Biotech Co., Ltd., Beijing, China). For mRNA analysis, the cDNA was made from total RNA by oligo-dT priming with a primeScript RT reagent kit (Tiangen Biotech Co., Ltd.) and the mRNA level of the following three genes (SRSF2, HIC2 and PLAU) was measured by qRT-PCR with gene-specific fluorescent Taqman probe together with the ft-actin using a different fluorescence-labeled probe (provided by ShingGene, Shanghai, China) in the FTC-3000P (FUNGLYN BIOTECH INC, Toronto, ON, Canada). For miR analysis, the cDNA was synthesized with the specific stem-loop primer and quantified by SYBR Green-based real-time PCR assay. Using the $2^{-\Delta\Delta Ct}$ method, the normalization with the U6 reads for miR or with β-actin for mRNA was performed before each's relative level between 5637 and H-bc was calculated.

Western Blotting Analysis

Cell lysates with 1×SDS loading buffer (60 mM Tris-HCl, pH6.8, 2% SDS, 20% glycerol, 0.25% bromphenol blue, 1.25%2-mercaptoethanol) were incubated at 100° C. for 10 min to facilitate the sample loading for the conventional western blotting analysis. The anti-SRSF2 (AP2800a), anti-HIC2 (AP18558c), anti-PLAU (AP8161b) and anti-GAPDH (AM1020a) were provided by Wuxi phama, Shanghai, China. The target proteins were then probed with anti-rabbit IgG peroxidase-conjugated antibody (LP1001b), or HRP goat anti-mouse IgG antibody (LP1002a) (All antibodies are from Abgent, San Diego, Calif., USA) followed by an enhanced chemiluminescence reaction (Thermo Fisher Scientific, Waltham, Mass., USA). The relative levels of proteins were quantified using densitometry with the Gel-Pro Analyzer (Media Cybernetics, Rockville, Md., USA). The target bands over the GAPDH band were densitometrically quantified and indicated under each band.

BSP Analysis

Genomic DNA was isolated by a standard phenol/chloroform purification method, qualified by electrophoresis on an agarose gel, treated by ammonium bisulfate-based bisulfite conversion method and the PCR fragments from the converted DNA was sequenced and analyzed. Raw sequence data files was processed and the area ratio (%) of C over C+T of the primary CpG dinucleotide was calculated as the percenatge of methylation and plotted.

The In Vivo Studies

Animal experiments were undertaken in accordance with the National Institutes of Health Guide for the Care and Use of Laboratory Animals. BALB/c male nude mice aged of 8-12 weeks were used for this study. 5637 or H-bc cells were embedded in BD Matrigel Matrix (Becton, Dickinson, Franklin Lakes, N.J., USA) and subcutaneously injected into the four sites at the back of mice as following: $1.7 \times 10^7$ cells/site for 5637, $0.7 \times 10^7$ cells/site for H-bc, 4 sites/mouse, 6 mice for 5637, 6 mice for H-bc, respectively. From the fourth day after cell injection, all 5637-generated tumors were intratumorally injected with 2 nM miR-193a-3p agomiR or miR-193a-5p agomiR, while H-bc-generated tumors were injected with 4 nM miR-193a-3p/-5p/Mock antagomiR/PBS in a similar manner. From the sixth day after cell injection, three mice from 5637 and three from H-bc intraperitoneally received Pa (45 ug/mouse) once in 2 days. The remaining six mice (three from 5637 and three from H-bc) received PBS as a mock treatment control. Mice were humanely killed on day 25, and the tumors were weighed and photographed. The tumor weight was described as the mean±S.D.

Expression levels of SRSF2, TP73 and Ki67 proteins were measured using immunochemical analysis on 5-mm slices of formalin-fixed paraffin-embedded tumor xenografts in nude mice. To avoid inter-treatment bias, the tissue slides from all the six groups were made on a single slide and subjected to the same immuno-staining simultaneously. Antigens were retrieved by pretreating dewaxed sections in a microwave oven at 750 Watts for 5 min in a citrate buffer (pH 6) processed with the Super Sensitive Link-Labeled Detection System (Biogenex, Menarini, Florence, Italy). The enzymatic activities were developed using 3-amino-9-ethylcarbazole (Dako, Milan, Italy) as a chromogenic substrate. Following counter staining with Mayer hematoxylin (Invitrogen), slides were mounted in an aqueous mounting medium (glycergel, Dako). Pictures were taken using the LEICA DM 4000B microscope (Wetzlar, Germany), while the relative level of each protein was calculated using the LEICA software (Wetzlar, Germany), and the percentage of the mock over the chemotherapeutic treated tumors was calculated and plotted.

Bioinformatics Analysis

R package pheatmap version 0.77 were used to create the diagrams. CpG island information for the human genome (hg19) was obtained from UCSC database. Differentially expressed miRs were calculated with in-house developed perl scripts. The networking analysis: the following eight genes: PLAU, HIC2, and SRSF2, together with the master transcription factor genes in each pathways (Oxidative stress: RBPJ, MYC/Max: MYC, Notch: NRF1, DNA damage: TP53 and NF-κB pathways: NFKB1) were used as seeds to extract from the known PPI from the STRING database version 9.10. The build-in one-step expand algorithm was used until a fully connected network of all seed genes were obtained. To simplify the model, the shortest paths between seeds were extracted from the networks. RNA-seq data (not shown) were used to identify the expression pattern of the model. To obtain the true functional role of each interaction in the connected network of eight seeds and four hub genes, the literature mining was performed by the STRING via full text reading, with both standard gene name and alternative name considered. Edges that are not consistent with our experimental data were removed from the network.

Statistical Analysis

Data are presented as means, and error bars indicate the S.D. or S.E. All statistical analyses were performed with Excel (Microsoft, Redmond, Wash., USA) or Prism (GraphPad Software Inc., La Jolla, Calif., USA). Two-tailed Student's t-test, a one-way analysis of variance or Mann-Whitney U test was used to calculate statistical significance. A P-value of <0.05 was considered to be significant.

Result

Expression of the DNA Methylation-Regulated miR-193a Gene Positively Correlates with the Multi-Chemoresistance of BCa Cells The drug dose for 50% cells killed by the following drugs: Pirarubicin (Pi), Paclitaxel (Pa), Adriamycin (Ad), and Epirubicin Hydrochloride (EH) after a treatment of 72 h, was determined in the following five BCa cell lines: 5637, T24, EJ, H-bc, and Biu87. Judged by the fold difference over the lowest $IC_{50}$, 5637 was the most multi-chemosensitive cell line, with the lowest $IC_{50}$ to four of five drugs, while H-bc was the most resistant cell line with its relative $IC_{50}$ by 8.32 to 36.96 folds higher than 5637 cells. From a RNA-seq based miR-omic analysis of 5637 and H-bc cell lines, 83 miRs were found differentially expressed by no less than two folds: 37 higher and 45 lower in 5637 than H-bc cells, respectively. Among the 20 miR genes that are co-localized with the CpG island, the miR-193a-3p differentially expressed between 5637 and H-bc cells at the top range in both RNA-seq omic and a qRT-PCR analysis. The hypermethylated state in 5637 and hypomethylated state in H-bc cells of the miR-193a gene suggested by the methyl-capture seq analysis were confirmed by a bisulfate conversion sequencing (BSP) analysis: It is hypermethylated in 5637 (the average CpG methylation: 78.6%) and barely methylated in H-bc (the average CpG methylation: 4.3%). In conclusion, the differential state of the miR-193a gene at both DNA methylation and expression levels tightly correlates with the multi-chemoresistance of BCa cells.

SRSF2, PLAU and HIC2 are Direct Targets of miR-193a-3p in BCa Cells

The number of the genes potentially regulated by one miR ranges from several hundreds to a couple of thousands. Among the predicted target genes of miR-193a-3p that were picked up by no less than three out of four commonly used predicting methods: miRDB (166 entries identified), miR base (380 entries), targets can (443 entries), target miner (243 entries), HIC2 (hypermethylated in cancer 2) gene, along with two known miR-193a-3p's targets: SRSF2 (serine/arginine-rich splicing factor 2) and PLAU (plasminogen activator, urokinase), were found to be expressed in an opposite manner of the miR-193a-3p at both RNA (RNA-seq based omic: and qRT-PCR analysis) and protein levels. Furthermore, a miR-193a-3p mimic transfection brought down the levels of all three genes in 5637 cells, and their levels were raised in the antagomiR-transfected H-bc cells.

For the proof that HIC2 and PLAU genes are direct targets of miR-193a-3p, both 3'-UTR regions were put at the downstream of the firefly luciferase gene in pGL3 (Promega, Madison, Wis., USA) to create pGL3-HIC2 UTR and pGL3-PLAU UTR constructs. Both constructs and pGL3 were transfected into 5637 and H-bc cells, respectively, for the functional state of miR-193a-3p in cells. Both UTR-contained constructs gave a significantly higher luciferase activity in 5637 than H-bc cells in an opposite pattern of miR-193a-3p's expression, in contrast to the no difference state of the pGL-3-resulted luciferase activities in both cell lines. Moreover, the miR-193a-3p mimic transfection repressed the luciferase activities of both 3'-UTR containing but not pGL-3 constructs in 5637 cells, and the reverse was found in the antagomiR-transfected H-bc cells. In conclusion, similar to SRSF2, both PLAU and HIC2 are the true direct targets of miR-193a-3p in BCa cells. The miR-193a-3p's effect on the BCa chemoresistance is likely to be realized by its repression of these three genes.

miR-193a-3p Rather than -5p Dictates the Multi-Chemoresistance of BCa Cells

Both SRSF2 and TP73 proteins were indeed significantly lower in H-bc than in 5637 cells (not shown) and were upregulated by the mimic transfection in 5637 and downregulated by the antagomiR transfection in H-bc cells, well matching the level (functional state too) of miR-193a-3p and -5p. A miR-193a-3p but not -5p mimic transfection are capable to reduce the drug-triggered cell death in 5637 cells by 0.2-1.3-fold in a drug-specific manner. The same conclusion was drawn from the analysis in the antagomiR-transfected H-bc cells. Therefore, miR-193a-3p but not -5p contributes to the BCa's multi-chemoresistance, although both express in a same pattern.

miR-193a-3p Regulates the Activities of the Chemoresistance-Associated Signaling Pathways in the Content of the BCa Multi-Chemoresistance For further mechanistic insights into the BCa chemoresistance, this example determined in both 5637 and H-bc cells the activities of the following 16 signaling pathways using the Qiagen's pathway reporter systems: Oxidative Stress, DNA Damage, NF-κB, Hypoxia, ER Stress, Heavy Metal Stress, Heat Shock, Glucocorticoid, JNK, Xenobiotic, Wnt, Notch, TGF-β, Cell Cycle/pRb-E2F, Myc/Max, and MAPK/ERK. Activities of seven pathways differed by more than two-folds between 5637 and H-bc cells, which might have a significant role in BCa chemoresistance. The pathways with higher activities in 5637 than in H-bc cells were DNA damage, NF-κB, Myc/Max and Heavy/Metal Stress pathways. The former three pathways were downregulated in the mimic-transfected 5637 cells and upregulated in the antagomiR-transfected H-bc cells. A reverse effect was observed on Oxidative Stress, Notch and Hypoxia pathways. The former two were activated in the mimic-transfected 5637 and repressed in the antagomiR-transfected H-bc cells. This example then individually repressed SRSF2, PLAU and HIC2 in 5637 cells by siRNA transfection for the impact on pathway activities. Only the activities of both Notch and Oxidative Stress were elevated in the SRSF2 siRNA-transfected 5637 cells. The pathways regulated by PLAU were DNA Damage, NF-κB and Myc/Max in a positive fashion.

The pathways regulated by HIC2 were Myc/Max in a positive fashion and Oxidative Stress/Notch signaling in a negative fashion. Compatible to the effect on the drug-triggered cell death, the influence of the miR-193a-3p's target genes on the pathways are in a gene-specific manner.

For the further mechanistic understanding, this example searched for the interactions among the three miR-193a-3p's targets (PLAU, SRSF2 and HIC2 genes) and the master transcription factor genes for these five signaling pathways: NRF1 for Oxidative stress, MYC for Myc/Max, RBPJ for Notch, TP53 for DNA Damage and NFKB1 for NF-κB pathways from the STRING database of the known protein-protein interactions (PPI) interactions. Using one-step direct path algorithm, a direct link between PLAU and TP53 (DNA-damage response pathway) or NFKB1 (NF-κB pathway) was shown. A direct physical interaction between TP53 and MYC protein (Myc/Max pathway), suggested by a proteomic analysis, may contribute to the PLAU's effect on the Myc/Max pathway. Via both literature mining and the expression analysis of these eight genes in the RNA-seq data sets of 5637 and H-bc cells, this example built a more sophisticated connection network. Three hub genes connecting both SRSF2 and PLAU to NRF1, RBPJ and TP53 genes, respectively, were all involved in the regulation of the acetylation state of both histones and non-histone proteins: PCAF (histone acetyltransferase b) and two histone deacetylases (HDAC6 and HDAC9). The hub gene connecting HIC2 protein to MYC (Myc/Max) pathway is CCNT1, encoding a CDK9-associated C-Type protein with a positive regulatory role in transcript elongation.

miR-193a-3p Promotes Both Growth and Pa Chemoresistance of the 5637- and H-Bc-Derived Tumor Xenografts in Nude Mice To minimize the inter-mouse bias, 5637 ($1.5\times10^7$ cells/site) or H-bc ($0.7\times10^7$ cells/site) cells were subcutaneously injected at the four back sites of each six mice each. An intratumor injection of miR-193a-3p/-5p agomiR/antagomiR or the scramble sequence control (Mock) or phosphate-buffered saline (PBS) into the 5637/H-bc-derived tumors was initiated on the fourth day and repeated four times once in 2 days. The intraperitoneal injection of PBS or Pa was started on day 6 into three mice each in either the 5637 or H-bc group and repeated four times once in 2 days. The tumor mass was weighed on day 25 at the end of this study. With half less cells injected, the H-bc-derived tumors were significantly heavier than 5637-derived tumors (0.81 g/0.53 g=1.53 in tumor weight), suggesting a miR-193a's promoting role for the in vivo in tumor growth. This conclusion was supported by the experiments where both 5637 and H-bc tumor xenografts were established in the same mice. An intratumor injection of miR-193a-3p but not -5p agomiR in comparison with the mock into the 5637 cell-derived tumor xenograft resulted in a bigger tumor mass of 5637 cell-derived tumor xenografts (0.81/0.53=1.53). The reverse observations were made from the antagomiR in H-bc tumor mice (0.13/0.40=0.33 in tumor weight).

Therefore, the miR-193a-3p but not -5p is capable to promote the in vivo tumor growth. Consistent with the observation that H-bc was more Pa-resistant than 5637 cells in cultured cells, an intraperitoneal injection of Pa caused the 5637 tumors in a much smaller size than the H-bc tumor: the tumor weight ratio of the Pa treated over PBS treated is 0.283 (5637) versus 0.40 (H-bc). To separate the tumor growth-promoting effects from the Pa resistance-enhancing effects, the tumor weights of the Pa group where miR-193a-3p, -5p and mock-transfected tumor xenografts were established in the same individual mice were compared. The ratios of tumor weight of the miR-193a-3p agomiR/Mock in 5637 mice (3.42) were greater than that in the -5p agomiR/Mock counterpart (1.57), indicating that miR-193a-3p compromised the Pa's tumor-inhibition capability. The same was concluded from the experiments with the antagomiR injection into the H-bc-derived tumor xenografts: the relative tumor weight of the -3p antagomiR/Mock (0.33) was smaller than that of the miR-193a-5p antagomiR/Mock: (1.1). Again, neither miR-193a-5p agomiR nor antagomiR altered the growth of the Pa-treated 5637 or H-bc tumors.

Further confirmation of the miR-193a's role in Pa resistance of BCa came from the immuno-histological analysis of SRSF2 (a miR-193a-3p's target), TP73 (a -5p's target) and Ki67 (an indicator for cell proliferation) in the tumor sessions of the Pa-treated versus PBS-treated mice. The intra-tumor injection of either miR-193a-3p or -5p's agomiR (into 5637)/antagomiR (into H-bc tumor) indeed led the expected changes of both SRSF2 or TP73 levels in tumor slides, which consolidate the conclusion that miR-193a-3p but not miR-193a-5p has a profound positive effect on both the growth and chemoresistance of the BCa cell-derived tumor xenografts in nude mice.

This example identified a miR-193a-3p centered axis that dictates the BCa's multi-chemoresistance, expression of which was under the negative control of the DNA methylation. Via its repressive effect on three target genes (and others) and in turn the five signaling pathways, the miR-193a-3p promotes the multi-chemoresistance (Pa, Pi, EH and Ad studied in this report) and the in vivo tumor growth of BCa cells. For further mechanistic insights, this example informatically identified the key links that connect miR-193a-3p via three of its target genes (SRSF2, PLAU and HIC2) to the five signaling pathways and therefore the chemoresistant phenotype of BCa cells. This study, therefore, provides a new set of diagnostic targets for the guided personalized chemotherapy of BCa.

Example 2. miR-193a-3p Regulates the Multi-Drug Resistance of Bladder Cancer by Targeting the LOXL4 Gene and the Oxidative Stress Pathway From detailed studies of a multi-chemosensitive (5637) versus a chemoresistant (H-bc) bladder cancer cell lines, this example demonstrates that miR-193a-3p [GenBank: NR_029710.1] promotes multi-chemoresistance of bladder cancer cells. This example further demonstrates that the lysyl oxidase-like 4 (LOXL4) gene [GenBank: NM_032211.6] is a direct target of miR-193a-3p and executes the former's impact on bladder cancer chemoresistance. The Oxidative Stress pathway activity is drastically affected by a forced reversal of miR-193a-3p or LOXL4 levels in cell and may act at the downstream of LOXL4 gene to relay the miR-193a-3p's impact on the multi-chemoresistance in both cultured cells and the tumor xenografts in nude mice. In addition to a new mechanistic insight, these results provide a set of the essential genes in this newly identified miR-193a-3p/LOXL4/Oxidative Stress axis as the diagnostic targets for a guided anti-bladder cancer chemotherapy. More details of this example can be found in Deng et al., "MIR-193A-3P REGULATES THE MULTI-DRUG RESISTANCE OF BLADDER CANCER BY TARGETING THE LOXL4 GENE AND THE OXIDATIVE STRESS PATHWAY," *Mol Cancer*, 13:234 (2014), the content of which is incorporated to the present disclosure by reference.

Methods

Cell Lines and Culture

Five bladder cancer cell lines were purchased from the Chinese Academy of Cell Resource Center (Shanghai, China): 5637 (ATCC NO. HTB-9), T24(ATCC NO. HTB-4), UM-UC-3 (ATCC NO. CRL-1749), Biu87 (established by department of Urology of Beijing Medical University in 1987) and H-bc cell lines (established by cancer research Institute of Kunming Medical College, 1986). UM-UC-3 cells are cultured in MEM plus 10% Fetal Bovine serum, and the other cell lines are cultured in RPMI1640 (Invitrogen, USA)+10% Fetal Bovine serum (Invitrogen, USA) and 1% glutamine at 37° C. in 5% $CO_2$.

Chemotherapeutics

The clinic grade of drugs are used (NCI Dictionary of Cancer Terms), Pirarubicin (Pi, Wanle, Shenzhen), Paclitaxel (Pa, Taiji, Sichuan), Adriamycin (Ad, Pfizer, Jiangsu), Epirubicin Hydrochloride (EH, Haizheng, Zhejiang), and Cisplatin (Ci, Haosen, Jiangsu).

Chemoresistance Profiling (IC50 Determination)

Cells at the logarithmic phase of growth were seeded in triplicate in 96-well plates at a density of $0.5 \times 10^4$/well and treated with 4 fold serious diluted drugs for 72 hours. The cell survival was then measured by a thiazolyl blue tetrazolium bromide (MTT, 490 nm reading)-based cell viability assay. Both the linear regression parameters and the $IC_{50}$ (the concentration of drug required for 50% cells killed) with the no-drug control as the reference were calculated. The relative chemoresistance was presented as the fold for the $IC_{50}$ of the cell lines over the lowest $IC_{50}$.

The Reagents for the Transient Transfection and In Vivoassays

All the mimic, agomiR, antagomiR, siRNA, the scramble sequence (negative control, NC) and the riboFECT CP transfection kit were supplied by Ribobio, Guangzhou, China. Transfection of both ribonucleic acid reagents mentioned above and the reporter plasmids was performed according to the manufactory's instruction. Chemically modified mimic oligonucleotides (agomir) were synthesized to regulate miR-193a-3p/5p expression in vivo. The 3' end of the oligonucleotides was conjugated to cholesterol, and all the bases were 2'-OMe modified. The agomir oligonucleotides were deprotected, desalted and purified by high-performance liquid chromatography.

The Luciferase Reporter Assay

A full length of the human LOXL4 3'-untranslated region (1325 bp) with a wide type and mutant target sequence for miR-193a-3p were cloned into 3' flank of luciferase coding sequence of pGL3 (Invitrogen, Carlsbad, Calif., USA) to construct pGL3-luc-LOXL4 WT and pGL3-luc-LOXL4 Mut, respectively. All the constructs were confirmed by DNA sequencing. Cells were seeded into 96-well plates at around $1 \times 10^4$ cells per well and transfected with a mixture of 50 ng pGL3-luc-LOXL4 WT or Mut, 5 ng Renilla plus 5 pmol mimic or NC nucleotides, with the riboFECT CP transfection kit according to the manufacturer's instruction. Both firefly and Renilla luciferase activities were measured around 18 hours after transfection by the Dual-Luciferase Reporter Assay System (Promega, Madison, Wis., USA) using a Promega GloMax 20/20 luminometer. The relative firefly luciferase activities were normalized with the Renilla luciferase activities, which served as an internal control for transfection efficiency for the standard analysis.

The Signaling Pathway Analysis

The following five signaling pathway reporter constructs were obtained from Qiagen (Hilden, German). DNA damage, Notch, NF-κB, Myc/Max and Oxidative Stress (OS) pathways and analyzed according to the manufacturer's instruction. Briefly, the cells were transfected in triplet with each firefly luciferase reporter construct in combination with the Renilla luciferase based control construct using the riboFECT CP transfection reagent, and both luciferase activities in cell extracts at 18 hours after transfection were measured. The relative luciferase activities (luciferase unit) of the pathway reporter over the negative control in the transfected cells were calculated as a measurement of the pathway activity.

Apoptosis Analysis

Cells were harvested and rinsed with PBS twice. Then 5 μl of FITC-labeled enhanced-annexinV and 5 μl (20 μg/ml) of propidium iodide were added into 100 μl cell suspension. Upon incubation in the dark for 15 min at room temperature, samples were diluted with 400 μl PBS. Flow cytometry was carried out on a FACS calibur instrument. The result was analyzed according to the manufacturer's instruction. The experiments were performed independently three times and a representative was shown.

RNA Analysis

Total RNA was isolated from the cells at the logarithmic phase by Trizol technology (Tiangen Biotech Co., Ltd., Beijing, China). For mRNA analysis, the cDNA primed by oligo-dT was made with a prime Script RT reagent kit (Tiangen Biotech Co., Ltd., Beijing, China) and the mRNA level of the genes LOXL4, SRSF2, Nrf-1,Nrf-2, CDC37, SUV39H1, and NQO1 were quantified by a duplex-qRT-PCR analysis where the Taqman probes in a different fluorescence for the β-actin (provided by Shing Gene, Shanghai, China) was used in the FTC-3000P PCR instrument (FUNGLYN BIOTECH INC, Toronto, Canada). Using the $2^{-\Delta\Delta Ct}$ method, the normalization with the β-actin level was performed before the relative level of the target genes was compared.

Bulge-Loop™ miRNA qRT-PCR

For detecting and quantifying the expression of specific miRNAs, RNA was reverse transcribed using Bulge-Loop™ miRNA qRT-PCR Primer Set (Ribobio) and quantified by the SYBR Green-based real-time PCR analysis in the FTC-3000P (FUNGLYN BIOTECH INC, Canada). The Ct values of the target miRs were normalized to the Ct values of U6 RNA before quantification using the $2^{-\Delta\Delta Ct}$ method.

Western Blot Analysis of Protein

Cells were lyzed with a lysis buffer (60 mM Tris-HCl, pH6.8, 2% SDS, 20% glycerol, 0.25% bromophenol blue, 1.25% 2-mercaptoethanol) and heated at 100° C. for 10 min before the electrophoresis/Western analysis. The anti-LOXL4 (AP17245b), anti-SRSF2 (AP2800a), anti-GAPDH (AM1020a), anti-rabbit IgG peroxidase-conjugated antibody (LP1001b), and HRP goat anti-mouse IgG antibody (LP1002a) were provided by Wuxiphama, Shanghai, China. The target bands were revealed by an enhanced chemiluminescence reaction (Thermo Fisher Scientific. Waltham, Mass., USA) and the relative density (level) of proteins over the GAPDH band were quantified with the Gel-Pro Analyzer (Media Cybernetics, Rockville, Md., USA).

The In Vivostudies

Animal experiments were undertaken in accordance with the National Institutes of Health Guide for the Care and Use of Laboratory Animals. BALB/c male nude mice of 8-12 weeks of age were used for this study. 5637 or H-bc cells were embedded in BD Matrigel™ Matrix (Becton, Dickinson, N.J., USA) and subcutaneously injected into at four sites at back of mice as following: $1.7 \times 10^7$ cells/site for 5637, $0.7 \times 10^7$ cells/site for H-bc,4 sites/mouse, 6 mice for 5637, 6 mice for H-bc, respectively. From the 4th day after cell injection, all 5637 generated tumors on the left back of nude mice were intratumorally injected with 2 nM miR-193a-3p agomiR/Mock, while H-bc generated tumors on the left back of nude mice were injected with 4 nM miR-193a-3p/Mock antagomiR. From the $6^{th}$ day after cell injection, 3 mice from 5637 and 3 from H-bc were intraperitoneally received Pa (45 ug/mouse) once in 2 days. The remaining 6 mice (3 from 5637 and 3 from H-bc) received phosphate-buffered saline (PBS) as a mock treatment control. Mice were humanely sacrificed on day 25, and the tumors were weighed and photographed. The tumor weight was described as the mean±S.D.

Expressions of SRSF2, LOXL4, and Ki67 proteins were measured using immunochemical analysis on 5-mm slices of formalin fixed paraffin-embedded tumor xenografts in nude mice. To avoid inter-treatment bias, the tissue slices from all the six groups were made on a single slide and subject to the same immuno-staining simultaneously. Antigens were retrieved by pretreating dewaxed sections in a microwave oven at 750 watts for 5 min in a citrate buffer (pH 6) processed with the Super Sensitive Link-Labeled Detection System (Biogenex, Menarini, Florence, Italy). The enzymatic activities were developed using 3-amino-9-ethylcarbazole (Dako, Milan, Italy) as a chromogenic substrate. Following counter staining with Mayer hematoxylin (Invitrogen), slides were mounted in aqueous mounting medium (glycergel, Dako). Pictures were taken using LEICA DM 4000B microscope (Wetzlar, German), while the relative level of each protein was calculated using LEICA software, percentage of the mock over the chemotherapeutic treated tumors was calculated and plotted.

Statistical Analysis

Data are presented as means, and error bars indicate the S.D. or S.E. All statistical analyses were performed with Excel (Microsoft, Redmond, Wash.) or Prism (GraphPad Software Inc., La Jolla, Calif.). Two-tailed Student's t-test, a one-way analysis of variance or Mann-Whitney U test was used to calculate statistical significance. A p-value of <0.05 was considered to be significant.

Results

The miR-193a-3p Level was Higher in the Chemoresistant (H-Bc and UM-UC-3) than the Chemosensitive (5637) BCa Cell Lines The dose required for 50% cells killed ($IC_{50}$) after a 72 hours drug treatment by Pirarubicin (Pi), Paclitaxel (Pa), Adriamycin (Ad), Cisplatin (Ci) or Epirubicin Hydrochloride (EH) were determined in the following five BCa cell lines: 5637, T24, Biu87, H-bc and UM-UC-3. Judged by the fold difference over the lowest $IC_{50}$, 5637 was the most multi-chemosensitive, while H-bc and UM-UC-3 were the most resistant cell lines. Revealed by both a sequencing based miRomic analysis and the qRT-PCR validation, the miR-193a-3p level was over 100 folds higher in both H-bc and UM-UC-3 than in 5637 cells. All these observations suggest that miR-193a-3p may have a promoting role in the BCa chemoresistance.

LOXL4 mRNA is a Direct Target of miR-193a-3p in BCa Cells

A given microRNA may regulate the expression of up to several hundred genes at the post-transcriptional level in both cellular content-dependent and sequence-specific manners. Besides SRSF2, miR-193a-3p's influence on the cancer chemoresistance is expected to be accomplished via repression of its other targets. To this end, this example checked the level of 359 Targetscan-predicted genes in the RNA-seq datasets (the RNA-seq omic data, not shown) of 5637, UM-UC-3 and H-bc cells. LOXL4 is one of several dozen genes that differentially expresses in a pattern opposite to the miR-193a-3p's. Further qRT-PCR and Western analyses showed that LOXL4 level is significantly higher in 5637 than in H-bc cells at both mRNA (RNA-seq based omic analysis: 1.00:0.08, and the qRT-PCR analysis: 1.00: 0.09) and protein levels (Western analysis: 1.00:0.54). The LOXL4 expression in another multi-chemoresistant cell line, UM-UC-3 cells was at an undetectable level.

This example further determined the LOXL4 level in both miR-193a-3p mimic transfected 5637 and the antagomiR transfected H-bc cells versus the mock transfected. In parallel with the changes of the miR-193a-3p level, a miR-193a-3p mimic transfection brought down the LOXL4 mRNA level by nearly 70% and the protein level by 58% in 5637 cells. As expected, a miR-193a-3p antagomiR transfection raised the mRNA level of LOXL4 by over 37 folds and the protein level by 84% in H-bc cells.

To conclude that LOXL4 gene is a direct target of miR-193a-3p, this example put the wild type or mutant 3'-UTR region (1325 bp) at the downstream of the firefly luciferase gene of pGL3 vector (Promega) to create pGL3-LOXL4 UTR WT and the PGL3-LOXL4 UTR Mut, respectively. Both constructs and pGL3 were transfected into 5637 and H-bc cells respectively, to determine whether the chemoresistance associated expression of miR-193a-3p in BCa cells is indeed functional. pGL3-LOXL4 UTR WT but not other two reporter constructs gave a significantly higher luciferase activity in 5637 than H-bc cells. Furthermore, the luciferase activity of pGL3-LOXL4-UTR WT but not other two was brought down by the mimic in 5637 cells and raised by the antagomiR transfection in H-bc cells. Getting all these together, LOXL4 is indeed, a direct target of miR-193a-3p and may execute the miR-193a-3p's effect on the BCa chemoresistance.

A siRNA Mediated LOXL4 Repression Essentially Reproduced the miR-193a-3p Mimic's Effect on the Chemoresistant State of 5637 Cells To explore the LOXL4 role in the BCa chemoresistance, this example transfected 5637 cells with the miR-193a-3p mimic and the siRNAs of SRSF2 and LOXL4, respectively, and assayed the cell death triggered by an $IC_{50}$ dosed drug. The cell death triggered by all the five drugs was significantly reduced in the miR-193a-3p mimic transfected 5637 cells. In parallel with the reduction of both target mRNA and protein levels, the siRNA mediated LOXL4 repression reduced the cell death triggered by four of five drugs, excluding Ad, while the siRNA mediated SRSF2 repression relieved the cell death triggered by four drugs, excluding Pi instead. These observations suggest that LOXL4 and SRSF2 have significantly overlapped but distinguished roles in execution of the miR-193a-3p's impact on the BCa chemoresistance in a drug-specific fashion. Furthermore, an additive (or synergistic) effect on both EH and Ad triggered cell death, but not on the other drugs were revealed in 5637 cells co-transfected by both siRNAs. Essentially as expected, a miR-193a-3p antagomiR transfection sensitized H-bc cells to the cell death triggered by four drugs, excluding Ci. As a measure of the successful transfection, the level of both LOXL4 and SRSF2 mRNAs was altered in a predicted direction in antagomiR transfected cells. In line with its negative effect on chemoresistance, a siRNA mediated LOXL4 repression lowered the percentage of apoptotic cells from 2.35% to 1.81%, an effect was not seen in the mimic transfected 5637 cells. Despite this difference, LOXL4 indeed plays an essential part in the miR-193a-3p's effect on the multi-chemoresistance of BCa cells, except for the Ad resistance.

It is surprising to find a significant discrepancy between the mRNA level (by qRT-PCR) and protein level (by Western blotting analysis) of SRSF2 and LOXL4 altered by miR-193-3p mimic or antagomiR, the alteration of the protein level is far limited than that of mRNA. It has been established that the relative contribution of a miR mediated translation repression and RNA degradation promotion to the expression of its target genes is target gene specific. Indeed, it has been shown that for highly repressed targets, mRNA destabilization usually comprised the major component of repression by miRs. Relevant to this issue, Wu, L et al. have recently shown that miRs also serves as a surveillance system to repress the expression of nonsense mRNAs that may produce harmful truncated proteins. It is thus likely that the observed massive reduction/increase of SRSF2 and LOXL4 mRNA by the mimic (in 5637 cells)/antagomiR in H-bc cells reflects mainly the changes in the nonsense transcripts in cells, which can not be translated to the protein at the first place.

The LOXL4 Level was Negatively Associated with the OS Pathway Activity in the Content of the BCa Chemoresistance For the mechanistic insights, this example used the Qiagen™ pathway reporter assay to compare the activities of the following five chemoresistance associated signaling pathways: DNA damage, Notch, NF-κB, Myc/Max and Oxidative Stress (OS) pathways in 5637 versus H-bc cells. The activities of the following three pathways: DNA damage, NF-κB and myc/max pathways were higher by no less than 2 folds in 5637 than H-bc cells. The activities of these three pathways were reduced in the miR-193a-3p mimic transfected 5637 and elevated in the antagomiR transfected H-bc cells, indicating a negative association of which with the BCa chemoresistance. The opposite was true for both OS and Notch pathways. This example then compared the pathway activities in the LOXL4 siRNAs versus the mock siRNA transfected 5637 cells. Although no or marginal effect on the activities of the DNA damage, NF-κB and Myc/Max pathways was observed, both OS and Notch pathways were activated in the LOXL4 siRNA transfected to a similar extent observed in the mimic transfected 5637 cells with the OS pathway's response most drastically. Therefore, the LOXL4's role to relay the miR-193a-3p's effect on the BCa chemoresistance is principally accomplished via its effect on the OS pathway.

This example further measured the mRNA levels of the genes encoding two master transcription factors in OS pathway: Nrf1 and Nrf2, one downstream gene of OS pathway: NQO1, and two LOXL4 interaction genes: CDC37 and SUV39H1 by qRT-PCR analysis. Coincidently, the Nrf1, Nrf2, NQO1 and SUV39H1 mRNAs were higher in H-bc than 5637 cells, and were raised in the miR-193a-3p mimic and LOXL4 siRNA transfected 5637 cells, while repressed in the miR-193a-3p antagomiR transfected H-bc cells. Although being slightly lower in H-bc than 5637 cells, the CDC37 level in 5637 cells was also significantly raised by the LOXL4 siRNA transfection. In conclusion, there is a very strong biochemical and biological link between the LOXL4 level and the OS pathway activity in the content of the BCa chemoresistance.

miR-193a-3p Promotes Pa Chemoresistance of BCa Viarepressing Both SRSF2 and LOXL4 Expression in BCa Tumor Xenografts in Nude Mice To minimize the inter-mouse bias, 5637 ($1.5 \times 10^7$ cells/site) or H-bc ($0.7 \times 10^7$ cells/site) cells were subcutaneously injected at two back sites of six mice each. An intratumor injection of miR-193a-3p agomiR/antagomiR into the 5637/H-bc derived tumors on the left back of mice was initiated on the $4^{th}$ day and repeated four times once in two days. The intraperitoneal injection of PBS or Pa was started on day $6^{th}$ into three mice each in either 5637 or H-bc groups and repeated four times once in two days. The tumor mass was weighed on day $25^{th}$. With half less cells injected, the H-bc derived tumors were significantly heavier than 5637 derived (0.81 g/0.53 g=1.53 in tumor weight), suggesting a miR-193a's promoting role in the in vivo tumor growth. This conclusion was supported by the experiments where both 5637 and H-bc tumor xenografts were established in the same mice. An intratumor injection of miR-193a-3p agomiR in comparison with the mock into the 5637 cell derived tumor xenograft resulted in a bigger tumor mass of 5637 cell derived tumor xenografts (0.81/0.53=1.53). The reverse was true from the compatible experiments with the antagomiR in H-bc tumor mice (0.13/0.40=0.33 in tumor weight). Therefore, the miR-193a-3p is capable to promote the in vivo BCa tumor growth in nude mice. In a full agreement with the observation that H-bc was more Pa-resistant than 5637 cells in cultured cells, an intraperitoneal injection of Pa reduced the 5637 tumors more dramatically than the H-bc tumor: the tumor weight ratio of the Pa treated over the PBS control is 0.283 (5637) versus 0.40 (H-bc).

This example further assayed the levels of SRSF2, LOXL4 and Ki67 (an indicator for cell proliferation) in the tumor sessions of the Pa-treated versus PBS-treated mice, by the immuno-histological analysis. The intratumor injection of either miR-193a-3p's agomiR (into 5637)/antagomiR (into H-bc tumor) indeed led the expected changes of both SRSF2 and LOXL4 proteins in tumor tissues, and consolidate the conclusion that miR-193a-3p promotes both the growth and chemoresistance of the BCa cell derived tumor xenografts in nude mice.

This study demonstrates that miR-193a-3p promotes the multi-chemoresistance of BCa via repressing of the LOXL4 expression and therefore activating the OS pathway. This study also provides a new set of genes in this newly identified miR-193a-3p/LOXL4/Oxidative Stress axis as the diagnostic targets for the guided anti-bladder cancer chemotherapy, including the level of the miR-193a-3p gene, both LOXL4 and SRSF2 gene and the key OS pathway associated genes in both cancer tissues and urine sediments.

Example 3. MiR-193a-3p Promotes the Multi-Chemoresistance of Bladder Cancer by Targeting the HOXC9 Gene Earlier examples have shown that miR-193a-3p promotes the multi-chemoresistance of bladder cancer cells via repressing its three target genes: SRSF2, PLAU and HIC2. This example shows that as a new direct target, the homeobox C9 (HOXC9) gene also executes the promoting effect of miR-193a-3p on the bladder cancer chemoresistance from a systematic study of multi-chemosensitive (5637) and resistant (H-bc) bladder cancer cell lines in both cell culture and tumor-xenograft/nude mice system. Paralleled with the changes in the drug-triggered cell death, the activities of both DNA damage response and oxidative stress pathways were drastically altered by a forced reversal of miR-193a-3p or HOXC9 levels in bladder cancer cells. In addition to a new mechanistic insight, these results provide a set of the essential genes in the miR-193a-3p/HOXC9/DNA damage response/oxidative stress pathway axis as the diagnostic targets for the guided anti-bladder cancer chemotherapy. More details of this example can be found in Lv et al., "MiR-193A-3P PROMOTES THE MULTI-CHEMORESISTANCE OF BLADDER CANCER BY TARGETING THE HOXC9 GENE," *Cancer Lett.* 357(1): 105-13 (2014), the content of which is incorporated to the present disclosure by reference.

Materials and Methods

Cell Lines

Bladder cancer cell lines were purchased from the Chinese Academy of Cell Resource Center (Shanghai, China): 5637 (ATCC NO. HTB-9) and H-bc cell lines (established by Cancer Research Institute of Kunming Medical College, 1986). Both cell lines are cultured in RPMI1640 (Invitrogen, USA)+10% Fetal Bovine serum (Invitrogen, USA) and 1% glutamine at 37° C. in 5% CO2.

Reagents for the Transient Transfection Assays

All the mimic, antagomiR, siRNA, the scramble sequence (negative control, NC) and the riboFECT CP transfection kit were supplied by Guangzhou Ribobio, China. Transfection of both ribonucleic acid reagents mentioned above and the reporter plasmids was performed according to the manufacturer's instruction.

Luciferase Reporter Assay

A full length of the human HOXC9 3'-untranslated region (UTR, 662 bp) with the target sequence for miR-193a-3p was cloned into 3' flank of the luciferase coding sequence of pGL3 (Invitrogen) to construct pGL3-luc-HOXC9 WT. All the constructs were confirmed by DNA sequencing. Cells were seeded into 96-well plates at around 1×104 cells per well and transfected with a mixture of 50 ng pGL3-luc-HOXC9 WT or Mut, 5 ng *Renilla* plus 5 pmol mimic or NC nucleotides, with the riboFECT CP transfection kit according to the manufacturer's instruction. Both firefly and *Renilla* luciferase activities were measured 18 hours after transfection by the Dual-Luciferase Reporter Assay System (Promega) using a Promega GloMax 20/20 luminometer.

Chemoresistance Profiling (IC50 Determination)

The clinic grades of drugs are used (NCI Dictionary of Cancer Terms), Pirarubicin (Pi, Wanle, Shenzhen), Paclitaxel (Pa, Taiji, Sichuan), Adriamycin (Ad, Pfizer, Jiangsu), Epirubicin Hydrochloride (EH, Haizheng, Zhejiang), and Cisplatin (Ci, Haosen, Jiangsu).

Apoptosis Analysis

Cells were harvested and rinsed with PBS twice. Then 5 µl of FITC-labeled enhancedannexinV and 5 µl (20 µg/ml) of propidium iodidewere added into 100 µl cell suspension. Upon incubation in the dark for 15 min at room temperature, sampleswere diluted with 400 µl PBS. Flow cytometry was carried out on a FACSCalibur instrument. The result was analyzed according to the manufacturer's instruction. The experiments were performed independently three times and a representative was shown.

RNA Analysis

Total RNA was isolated from the cells at the logarithmic phase by Trizol technology (Tiangen Biotech Co., Ltd., Beijing, China). For the mRNA analysis, the cDNA primed by oligo-dT was made with a prime Script RT reagent kit (Tiangen Biotech Co., Ltd., Beijing, China) and the mRNA level of the genes HOXC9 was quantified by a duplex-qRT-PCR analysis where the Taqman probes in a different fluorescence for the β-actin (provided by Shing Gene, Shanghai, China) were used in the FTC-3000P PCR instrument (Funglyn Biotech Inc, Canada). Using the 2-ΔΔCt method, the normalization with the β-actin level was performed before the relative level of the target genes was compared.

Bulge-Loop™ miRNA qRT-PCR

For detecting and quantifying the expression of specific miRNAs, RNA was reverse transcribed using Bulge-Loop™ miRNA qRT-PCR Primer Set (Ribobio) and quantified by the SYBR Green-based real-time PCR analysis in the FTC-3000P (FUNGLYN BIOTECH INC, Canada). The Ct values of the target miRs were normalized to the Ct values of U6 RNA before quantification using the 2-ΔΔCt method.

Western Blot Analysis of Protein

Cells were lysed with a lysis buffer (60 mM Tris-HCl, pH 6.8, 2% SDS, 20% glycerol, 0.25% bromophenol blue, 1.25% 2-mercaptoethanol) and heated at 100° C. for 10 min before the electrophoresis/Western analysis. The anti-HOXC9 (10665-1-AP) was purchased from proteintech, and anti-GAPDH (AM1020a), anti-rabbit IgG peroxidase-conjugated antibody (LP1001b), and HRP goat anti-mouse IgG antibody (LP1002a) were provided by Wuxiphama, Shanghai, China. The target bands were revealed by an enhanced chemiluminescence reaction (Pierce) and the relative density (level) of proteins over the GAPDH band were quantified with the Gel-Pro Analyzer (Media Cybernetics).

The In Vivo Studies

Expressions of HOXC9 protein were measured using immunochemical analysis on 5-mm slices of formalin fixed paraffin-embedded tumor xenografts in nude mice. To avoid inter-treatment bias, the tissue slides from all the six groups were made on a single slide and subjected to the same immuno-staining simultaneously. Antigens were retrieved by pretreating dewaxed sections in a microwave oven at 750 watts for 5 min in a citrate buffer (pH 6) processed with the Super Sensitive Link-Labeled Detection System (Biogenex, Menarini, Florence, Italy). The enzymatic activities were developed using 3-amino-9-ethylcarbazole (Dako, Milan, Italy) as a chromogenic substrate. Following counterstaining with Mayer hematoxylin (Invitrogen), slides were mounted in aqueous mounting medium (glycergel, Dako). Pictures were taken using a LEICA DM 4000B microscope, while the relative level of each protein was calculated using LEICA software, percentage of the mock over the chemotherapeutic treated tumors was calculated and plotted. The animal study proposal was approved by the Institutional Animal Care and Use Committee (IACUC) of the Harbin Medical University with the permit number: SYXK(Hei)2011-022. All mouse experimental procedures were performed in accordance with the Regulations for the Administration of Affairs Concerning Experimental Animals approved by the State Council of People's Republic of China.

Statistical Analysis

Data are presented as means, and error bars indicate the S.D. or S.E. All statistical analyses were performed with Excel (Microsoft, Redmond, Wash.) or Prism (GraphPad Software Inc., La Jolla, Calif.). Two-tailed Student's t-test, a one-way analysis of variance or Mann-Whitney U test was used to calculate statistical significance. A p-value of <0.05 was considered to be significant.

Results

The HOXC9 is a Direct Target of miR-193a-3p in BCa Cells

The miR-193a-3p level is significantly lower in a multi-chemosensitive (5637) than a multi-chemo resistant (H-bc) BCa cell line, but the reverse is true for the level of its three target genes SRSF2, HIC2 and PLAU, suggesting the critical role of the former in execution of the miR-193a-3p's chemoresistance impact. For other targets of miR-193a-3p that are instrumental to the BCa multi-chemoresistance, we examined the expression pattern of the bioinformatically suggested candidates (221) of miR-193a-3p by TargetScan software (http://www.targetscan.org/) between 5637 and H-bc cell lines in the RNA-seq omic dataset and selected the HOXC9 gene for further mechanistic study. The BCa chemoresistance associated expression of the HOXC9 gene was confirmed by qRT-PCR assay at steady state mRNA level and Western blot analysis at the protein level. Its level was higher in 5637 than H-bc cells at both protein (1.00: 0.36) and mRNA levels (qRT-PCR analysis: 1.00:0.71). This example then determined the HOXC9 level in the miR-193a-3p mimic transfected 5637 and the antagomiR transfected H-bc cells versus the NC (scramble sequence control) transfected. Following the changes of the miR-193a-3p level, a miR-193a-3p mimic transfection brought down the HOXC9 mRNA to nearly 38% and protein to 76% of that in the NC transfected 5637 cells.

As expected, miR-193a-3p antagomiR transfection raised the mRNA level of HOXC9 to 183% and the protein level by 230% in H-bc cells. To conclude whether the HOXC9 is a direct target of miR-193a-3p, we put the full length (662 bp) of HOXC9 3'-untranslated region (UTR) at the downstream of the firefly luciferase gene of pGL3-control vector (Promega) to create pGL3-HOXC9 UTRWT construct. Both pGL3-HOXC9 UTRWT and pGL3 enhancer control were transfected into 5637 and H-bc cells respectively, to determine whether the differentially expressed miR-193a-3p in BCa cells of distinct chemoresistance is really functional. pGL3-HOXC9-UTRWT but not pGL3 gave a significantly higher luciferase activity in 5637 than in H-bc cells. Furthermore, the luciferase activity of pGL3-HOXC9-UTR WT was brought down in the mimic transfected 5637 and raised in the antagomiR transfected H-bc cells but not in the pGL3 transfected control. Getting all these together, HOXC9 is indeed a direct target of miR-193a-3p and may execute the miR-193a-3p's effect on BCa chemoresistance.

A forced reversal of the HOXC9 level substantially reproduced the miR-193a-3p mimic's effect on the BCa chemoresistance. A functional connection of the miR-193a-3p with a HOXC9's role in the BCa multi-chemoresistance was initially suggested by the observation that both HOXC9 mRNA and protein were reduced in the both miR-193a-3p mimic and HOXC9 siRNA transfected cells, where the cell death triggered by all five drugs tested were eased by miR-193a-3p mimic. However, a HOXC9 siRNA transfection only desensitized 5637 cells to the cell death triggered by Ci, EH or Pi. Conversely, along with the rise of HOXC9 protein by miR-193a-3p antagomiR, H-bc cells became more amenable to the cell death triggered by the following four drugs: Pi, Pa, Ad or EH. Consistent with the results in 5637 cells, a transfection of the GFP-tagged HOXC9 expression construct sensitizes H-bc cells to EH, Ci or Pi, but not the other two drugs. A siRNA mediated HOXC9 repression also lowered the percentage of apoptotic cells from 2.35% to 2.11% in 5637 cells, in contrast with a mild effect by the miR-193a-3p mimic transfection. However, the G2-arresting effect by miR-193a-3p mimic was not seen in 5637 cells transfected by the GFP-tagged HOXC9 expression construct. The reasons for this disparity remain to be explored. Nevertheless, HOXC9 does mediate the miR-193a-3p's promoting effect on both EH and Pi chemoresistance of BCa cells to a significant extent.

The HOXC9 gene positively regulates both DNA damage response and oxidative stress pathways in the context of the EH and Pi-resistance of BCa cells.

The earlier examples have shown that miR-193a-3p regulates the multi-chemoresistance via repressing the expression of three of its downstream targets: SRSF2, PLAU and HIC2 and in turn altering the activities of the following five signaling pathways: DNA damage response, Notch, NF-κB, Myc/Max and Oxidative Stress. Therefore, this example then checked which of these five pathways are also affected in both 5637 and H-bc cells, where the HOXC9 level was forced reversed.

Parallel with the reduced expression of the HOXC9 gene by miR-193a-3p mimic or HOXC9 siRNA transfection, and the activities of the following four pathways: DNA damage response, NF-κB, Myc/Max and Oxidative stress in 5637 cells, except for the Notch pathway also went down in an expected fashion but the relative potency differed. For instance, the activity of DNA damage response pathway was reduced by HOXC9 siRNA to 87%, in contrast to 17%, of the NC level by the miR-193a-3p mimic. This example then assessed the changes of the mRNA levels of the following genes in the same set of 5637 cells: the downstream genes of DNA damage response pathway (CDKN1A and EDN1), NF-κB (RelA), myc/max pathway (TERT and ODC1) and Oxidative stress pathway (NQO1,SUV39H1, ECSIT, HO-1 and key transcriptional factor of Oxidative stress pathway Nrf2), as well as HOXC9 by qRT-PCR analysis. Along with the reduction of the HOXC9 mRNA by siRNA, EDN1 and ODC1 mRNA level went down and all Oxidative stress pathway related genes were activated as correlated with the effect of miR-193a-3p mimic, while leaving the expression of other pathway related genes intact or affected in a manner opposite to that for the miR-193a-3p mimic (i.e. RelA and TERT). Therefore, the HOXC9 connection to miR-193a-3p is most likely attributed to its effects on the activities of DNA damage response and oxidative stress pathways but not the other three pathways.

This example further transfected H-bc cells with a GFP-HOXC9 expression construct or a GFP construct and tested the activities of these five pathways in H-bc cells. Among the four pathways affected in the siRNA transfected 5637 cells, only the activities of DNA damage response and oxidative stress pathway reversed drastically by both miR-193a-3p antagomiR and EGP-HOXC9. Therefore, HOXC9's role to relay miR-193a-3p's effect on BCa chemoresistance is principally accomplished via its effect on DNA damage response and oxidative stress pathways.

The HOXC9 expression was reduced in the miR-193a-3p agomiR-injected 5637 tumor xenografts and raised in the antagomiR-injected H-bc tumor xenografts in nude mice. In the previous example, it was shown that miR-193a-3p promotes Pa chemoresistance of BCa in tumor xenografts of nude mice via the repression of three of its targets in tumor tissues: SRSF2, PLAU and HIC2. Here, this example semi-quantified the levels of HOXC9 protein in the same set of the xenografts by immuno-histological analysis. The intratumor injection of either miR-193a-3p's agomiR (into 5637)/antagomiR (into H-bc tumor) indeed led to the expected changes in the HOXC9 protein in the tumor tissues.

This observation further supports the notion that the HOXC9 gene is the direct target of miR-193a-3p and may execute the miR-193a-3p's promoting effect in the Pa-chemoresistance of the BCa cells.

In conclusion, this example identified HOXC9, as a newly defined target of miR-193a-3p, which relays the former's impact on the multi-chemoresistance in BCa cells along with its multiple other targets, mainly through regulating the activity of the DNA damage response and oxidative stress pathways.

Example 4. The miR-193a-3p Regulated PSEN1 Gene Suppresses the Multi-Chemoresistance of Bladder Cancer This example shows that, among the differentially expressed genes between the chemosensitive (5637) and chemoresistant (H-bc) bladder cancer cell lines, the expression level of the PSEN1 gene (presenilin 1), a key component of the γ-secretase, is negatively correlated with chemoresistance. A small interfering RNA mediated repression of the PSEN1 gene suppresses cell apoptosis and de-sensitizes 5637 cells, while overexpression of the presenilin 1 sensitizes H-bc cells to the drug-triggered cell death. As a direct target of microRNA-193a-3p that promotes the multi-chemoresistance of the bladder cancer cell, PSEN1 acts as an important executor for the microRNA-193a-3p's positive impact on the multi-chemoresistance of bladder cancer, probably via its activating effect on DNA damage response pathway. In addition to the mechanistic insights, the key players in this microRNA-193a-3p/PSEN1 axis are likely the diagnostic and/or therapeutic targets for an effective chemotherapy of bladder cancer. More details of this example can be found in Deng et al., "THE MIR-193A-3P REGULATED PSEN1 GENE SUPPRESSES THE MULTI-CHEMORESISTANCE OF BLADDER CANCER," *Biochim Biophys Acta.* 1852(3):520-8 (2015), the content of which is incorporated to the present disclosure by reference.

Materials and Methods

Cell Lines and Transfection

Cell lines—5637 (ATCC NO. HTB-9) and H-bc (established by cancer research Institute of Kunming Medical College, 1986.) were purchased from the Chinese Academy of Sciences Committee on Culture Collection Cell Bank, Shanghai Institutes for Biological Sciences, Chinese Academy of Cell Resource Center. Both cell lines are cultured in RPMI1640 (Invitrogen, USA)+10% fetal bovine serum (Invitrogen, USA) and 1% glutamine at 37° C. in 5% $CO_2$.

The Mimic/antagomiR/siRNA/Overexpression Plasmid Transfection

All the mimic, agomiR, antagomiR, siRNA and the scramble sequence control (NC) as well as the ribo FECT CP transfection kit were supplied by Guangzhou Ribobio, China). The mammalian expression constructs for PSEN1 (EX-G0389-M98-5) with GFP tag were supplied by Guangzhou Fulengen, China. Transfection of both ribonucleic acid reagents mentioned above and the reporter plasmids in a Cignal Finder Pathway Reporter package (Qiangene, US) was performed according to the manufacturer's instruction. Chemicallymodifiedmimic oligonucleotides (agomir) were synthesized to regulate miR-193a-3p/5p expression in vivo. The 3' end of the oligonucleotides was conjugated to cholesterol, and all the bases were 2'-OMe modified. The agomir oligonucleotides were deprotected, desalted and purified by high-performance liquid chromatography.

Chemotherapeutics

All the chemotherapeutic drugs used are of the clinic grade (NCI Dictionary of Cancer Terms), pirarubicin (Pi, Wanle, Shenzhen), paclitaxel (Pa, Taiji, Sichuan), adriamycin (Ad, Pfizer, Jiangsu), epirubicin hydrochloride (EH, Haizheng, Zhejiang), and cisplatin (Ci, Haosen, Jiangsu). The chemo-resistance profiling (IC50 measurements) was conducted as previously described.

Analysis of RNA

Total RNA was isolated using a TRIzol reagent (Tiangen Biotech Co., Ltd., Beijing, China). For mRNA analysis, the cDNA was made from total RNA by oligo-dT priming with a prime Script RT reagent kit (Tiangen Biotech Co., Ltd., Beijing, China) and the steady state mRNA level expression of PSEN1 was measured by qRT-PCR with gene-specific fluorescent Taqman probe together with the β-actin using a differentially fluorescence-labeled probe (provided by Shing Gene, Shanghai, China) in the FTC-3000P (Funglyn Biotech Inc., Canada). Using the 2-ΔΔ Ct method, the normalization with β-actin was performed before each's relative level between 5637 and H-bc was calculated.

Analysis of Protein

Cells lysate with 1×SDS loading buffer (60 mMTris-HCl, pH 6.8, 2% SDS, 20% glycerol, 0.25% bromphenol blue, 1.25% 2-mercaptoethanol) was heated at 100° C. for 10 min to facilitate the sample loading for the conventional Western analysis. The anti-PSEN1 (AJ1650a), anti-α-tubulin (AJ1034a) and anti-GAPDH (AM1020a) were provided by Wuxi Pharma, Shanghai, hina. The target proteins were then probed with anti-rabbit IgG peroxidase-conjugated antibody (LP1001b), or HRP goat anti-mouse IgG antibody (LP1002a) (all antibodies are from Abgent, San Diego, Calif.) followed by an enhanced chem-illuminescence reaction (Pierce). The relative levels of proteins were quantified using densitometry with the Gel-Pro Analyzer (Media Cybernetics). The target bands over the GAPDH or α-tubulin band were densitometrically quantified and indicated under each band.

Analysis of Cell

Apoptosis Analysis

Every group of cells was harvested and diluted with PBS twice. Then 5 μl of FITC-labeled enhanced-annexin V and 5 μl of 20 μg/ml of propidium iodide were added to 100 μl cell. Upon incubation in the dark for 15 min at room temperature, samples were diluted with 400 μl PBS. Flow cytometry was carried out on a FACSCalibur instrument. The result was analyzed by random software. The experiments were performed independently three times.

The Luciferase Reporter Assay

A full length of the human PSEN1 3'-untranslated region (1112 bp) with the miR-193a-3p targeting sequence (WT) or mutant target sequence (Mut) were cloned at the downstream of the firefly luciferase gene in pGL3 (Invitrogen) to construct pGL3-luc-PSEN1. All the constructs were confirmed by restriction digestion.

In Vivo Study

The xenograftmodel on nude mice was generated and analyzed. Expressions of PSEN1 protein were measured using immunochemical analysis on 5-mm slices of formalin fixed paraffin-embedded tumor xenografts in nude mice. To avoid inter-treatment bias, the tissue slides from different groups were made on a single slide and subject to the same immuno-staining simultaneously. Antigens were retrieved by pretreating dewaxed sections in a microwave oven at 750 W for 5 min in a citrate buffer (pH 6) processed with the Super sensitive link-labeled detection system (Biogenex, Menarini, Florence, Italy). The enzymatic activities were developed using 3-amino-9-ethylcarbazole (Dako, Milan, Italy) as a chromogenic substrate. Following counter staining with Mayer hematoxylin (Invitrogen), slides were mounted in aqueous mounting medium (glycergel, Dako). Pictures were taken using LEICA DM 4000B microscope, while the relative level of each protein was calculated using LEICA software, and the percentage of themock over the chemotherapeutic treated tumors was calculated and plotted.

Statistical Analysis

Data are presented as means, and error bars indicate the S.D. or S.E. All statistical analyseswere performedwith Excel (Microsoft, Redmond, Wash.) or Prism (GraphPad Software Inc., La Jolla, Calif.). Two-tailed Student's t-test, a one-way analysis of variance or Mann-Whitney U test was used to calculate statistical significance. A P value of <0.05 was considered to be significant.

Results

PSEN1 is a Negative Regulator of the Multi-Chemoresistance of BCa

Among 9051 differentially expressed genes between a multi-chemosensitive (5637) versus a resistant BCa cell line (H-bc) by the RNA-seq based omic analysis, the PSEN1 gene was selected for further study. Its level was higher in 5637 than H-bc cells at both protein (4.09:1) and mRNA levels (RNA-seq based omic: 2.25:1, and qRT-PCR analysis: 1.92:1).

To demonstrate its role in the BCa chemoresistance, this example suppressed the PSEN1 expression in 5637 cells by siRNA and found that the cell death triggered by each of the five drugs (paclitaxel, Pa; adriamycin, Ad; cisplatin, Ci; pirarubicin, Pi; epirubicin hydrochloride, EH) were suppressed in the PSEN1 siRNA transfected 5637 cells. Conversely, an over-expressed GFP-tagged PSEN1 protein (by Western analysis and an immunofluorescence analysis) sensitized H-bc cells to Ad, Ci, Pi, or EH, but not Pa.

The PSEN1 is a Direct Target of miR-193a-3p in BCa Cells

MiR-193a-3p has been noted for its role in the multichemoresistance in both HCC and BCa cells. The miR-193a-3p level is significantly lower in 5637 than in H-bc, while its target genes SRSF2, HIC2 and PLAU levels are lower in H-bc than 5637 cells, a same expression pattern of the PSEN1 gene in the context of the multi-chemoresistance of BCa. Incidentally, miR-193a-3p is one of 56 miRs that are bioinformatically capable by the TargetScan software of repressing the PSEN1 gene expression at the post-transcriptional level. To check the PSEN1 status as one of the miR-193a-3p's targets, hit example determined the PSEN1 level in the miR-193a-3p mimic transfected 5637 and antagomiR transfected H-bc cells versus the scramble sequence control (NC) transfected. Following the changes of the miR-193a-3p level (up to roughly 4000 folds bymimic and 0.4% by antagomiR relative to the NC), the miR-193a-3p mimic transfection brought down the PSEN1mRNA to 52% and the protein to 88% of the NC transfected 5637 cells. As expected, a miR-193a-3p antagomiR transfection raised the mRNA level of PSEN1 by roughly 5 folds and the protein level by 147% of the NC level in H-bc cells.

To determine whether the PSEN1 is a direct target of miR-193a-3p, this example put the full length wild type or mutant 3'-untranslated region (UTR) mega) to create pGL3-PSEN1 UTR WT or the PGL3-PSEN1 UTR Mut. Both constructs and pGL3-control were transfected into 5637 and H-bc cells, respectively, to determine whether the differentially expressed miR-193a-3p in the context of the chemoresistance BCa cells is really functional. pGL3-PSEN1-UTR WT but none of other two reporter constructs gave a significantly higher luciferase activity in 5637 than in H-bc cells. Furthermore, the luciferase activity of pGL3-PSEN1-UTR WT but not other two was brought down in the mimic transfected 5637 cells and raised in the antagomiR transfected H-bc cells.

Following the changes of the PSEN1 protein level in both the miR-193a-3p mimic and PSEN1 siRNA transfected 5637 cells, the cell death triggered by all five drugs was reduced. Conversely, a transfection of the GFP-tagged PSEN1 expression construct raised the PSEN1 protein level, sensitized H-bc cells to Ad, Pi, or EH. In line with its negative effect on chemoresistance, a siRNA mediated PSEN1 repression reduced the apoptotic cells from 2.35% to 1.36%, an effect that was not seen in the mimic transfected 5637 cells, the interpretation remains to be found. Nevertheless, the PSEN1 gene seems to have a negative role opposite to the miR-193a-3p's positive effect on the multichemoresistance of BCa cells. Getting all these observations together, PSEN1 executes to a great extent the miR-193a-3p's effect on the BCa chemoresistance to all five drugs according to the results in the transfected 5637 cells or the following three drugs: Ad, Pi and EH according to the results in the transfected H-bc cells.

PSEN1 Positively Regulates the DNA Damage Response Pathway in the Context of BCa Multi-Chemoresistance Earlier examples showed that miR-193a-3p regulates the multi-chemoresistance via repressing three of its downstream targets: SRSF2, PLAU and HIC2 and in turn altering the activities of following five signaling pathways: DNA damage response, Notch, NF-κB, Myc/Max and oxidative stress. Therefore, this example determined which of these five pathways are also affected by the forced changes of PSEN1 level in both 5637 and H-bc cells. When the PSEN1 level was repressed by either miR-193a-3p mimic or PSEN1 siRNA transfection, activities of the DNA damage response and Myc/Max pathways were affected. For instance, the activity of the DNA damage response pathway was reduced by PSEN1 siRNA to 85% of the level in the NC transfected control, in contrast to 17% of the NC level by the miR-193a-3p mimic. For the Myc/Max pathway, the PSEN1 siRNA led to a greater repression than the miR-193a-3p mimic.

This example further assessed the changes of the mRNA levels of the following genes in 5637 cells transfected by the PSEN1 siRNA in comparison with the NC and miR-193a-3p mimic: the downstream genes of the Myc/Max pathway (TERT and ODC1) and of the DNA damage response pathway (CDKN1A and EDN1) as well as three members of γ-secretase: PSEN1/2 and APH1A by qRT-PCR analysis. Along with the reduction of the PSEN1 mRNA by miR-193a-3p mimic or PSEN1 siRNA, one of the downstream targets of the Myc/Max pathway, ODC1 mRNA level was reduced as expected. However, the PSEN1 siRNA raised the mRNAs of the DNA damage response pathway targets rather than repressed by the mimic in 5637 cells. One plausible explanation for this conflicting observation is that the repression of these two downstream genes by miR-193a-3p is not achieved via its repression of PSEN1 expression at the post-transcriptional level. Intriguingly, miR-193a-3p mimic transfection not only brought down the PSEN1 level, but also PSEN2 and APH1A levels. A PSEN1 independent mechanism may account for the seeming conflicting results in the context of BCa multi-drug chemoresistance.

This example further compared the activities of these five pathways in the H-bc cells transfected with a GFP-PSEN1 expression construct or a GFP alone construct and showed that among the two pathways suggested by the tests in 5637 cells, only the activity of the DNA damage response pathway was raised drastically by both miR-193a-3p antagomiR and EGPPSEN1. Therefore, the PSEN1's role to relay the miR-193a-3p's effect on the BCa chemoresistance is principally accomplished via its effect on the DNA damage response pathway.

PSEN1 Expression was Reduced in the miR-193a-3p agomiR Injected 5637 Tumor Xenografts and Raised in the antagomiR-Injected H-Bc Tumor Xenografts.

Recently, it has been shown that miR-193a-3p promotes the Pa chemoresistance of BCa in tumor xenografts of nude mice via its repression of three of its targets in tumor tissues: SRSF2, PLAU and HIC2. The present study semi-quantified by an immuno-histological analysis of the levels of PSEN1 protein in the same set of the tumor tissues in the mice that were subjected to an injection of Pa or PBS. The intratumor injection of either miR-193a-3p's agomiR (into 5637)/antagomiR (into H-bc tumor) indeed led to the expected changes of the PSEN1 protein in the tumor tissues. This observation further supports the notion that PSEN1 gene has a role in the miR-193a-3p's promoting effect in the Pa-chemoresistance of the BCa cells.

DNA methylation analysis of the promoter region of the following 11 genes: SALL3, CFTR, ABCC6, HPR1, RASSF1A, MT1A, RUNX3, ITGA4, BCL2, ALX4, MYOD1, DRM, CDH13, BMP3B, CCNA1, RPRM, MINT1, and BRCA1, in urine sediments confirmed the existing diagnosis of 121 among 132 bladder cancer cases (sensitivity, 91.7%) with 87% accuracy. In this study, the data here show that PSEN1 is a direct target of miR-193a-3p, and negatively regulates the multi-chemoresistance of BCa by activation of the DNA damage response pathway. Therefore, the DNA methylation state of the miR-193a gene and expression state of both PSEN1 gene the DNA damage response pathway associated genes in both cancer tissues and urine sediments should be promising diagnostic targets for the guided anti-bladder cancer chemotherapy.

Example 5. The miR-193a-3p-Regulated ING5 Gene Activates the DNA Damage Response Pathway and Inhibits Multi-Chemoresistance in Bladder Cancer It was shown that the bladder cancer (BCa) cell line 5637 is significantly more sensitive to the cytoxicity of five chemotherapeutic agents than H-bc cells. Using an RNA-seq-based omic analysis and validation at both the mRNA and protein levels, this example found that the inhibitor of growth 5 (ING5) gene was upregulated in 5637 cells compared with H-bc cells, indicating that it has an inhibitory role in BCa chemoresistance. siRNA-mediated inhibition of ING5 increased the chemoresistance and inhibited the DNA damage response pathway in 5637 cells. Conversely, forced expression of EGFP-ING5 decreased the chemoresistance of and activated the DNA damage response pathway in H-bc cells. We also showed that ING5 gene expression is inhibited by miR-193a-3p and is instrumental in miR-193a-3p's role in activating BCa chemoresistance. Our results demonstrate both the role and mechanism of inhibition of BCa chemoresistance by ING5. More details of this example can be found in Deng et al., "THE MIR-193A-3P-REGULATED ING5 GENE ACTIVATES THE DNA DAMAGE RESPONSE PATHWAY AND INHIBITS MULTI-CHEMORESISTANCE IN BLADDER CANCER," *Oncotarget*, 6(12):10195-206 (2015), the content of which is incorporated to the present disclosure by reference.

Methods

Cell Lines

BCa cell lines were purchased from the Chinese Academy of Cell Resource Center (Shanghai, China): 5637 (ATCC NO. HTB-9) and H-bc (established by the Cancer Research Institute of Kunming Medical College, 1986). Both cell lines were cultured in RPMI 1640 (Invitrogen, USA) plus 10% fetal bovine serum (Invitrogen, USA) and 1% glutamine at 37° C. in 5% $CO_2$.

Reagents for the Transient Transfection Assays

The mimic, agomiRs, antagomiRs, siRNAs, the scrambled sequence (negative control, NC) and the riboFECT CP transfection kit were supplied by Ribobio (Guangzhou, China). The GFP-tagged overexpression ING5 construct (construct from pReciever-M98) was purchased from Genecopia, (Guangzhou, China). Transfection of both the ribonucleic acid reagents mentioned above and the reporter plasmids was performed according to the manufacturer's instructions.

Chemically modified mimic oligonucleotides (agomiRs) were synthesized to regulate miR-193a-3p/5p expression in vivo. The 3' end of the oligonucleotides was conjugated to cholesterol, and all of the bases were 2'-OMe modified. The agomiR oligonucleotides were deprotected, desalted and purified by high-performance liquid chromatography.

Luciferase Reporter Assay

A full-length human ING5 3'-UTR (1037 bp) with a wild-type or a mutant target sequence for miR-193a-3p was cloned into the 3' flank of the luciferase coding sequence of pGL3 (Invitrogen) to construct pGL3-luc-ING5 WT or pGL3-luc-ING5 Mut, respectively. All of the constructs were confirmed by DNA sequencing. Cells were seeded into 96-well plates at approximately $1 \times 10^4$ cells per well and transfected with a mixture of 50 ng of pGL3-luc-ING5 WT or Mut, 5 ng of *Renilla* plus 5 pmol of mimic or NC nucleotide using the riboFECT CP transfection kit according to the manufacturer's instructions. Both the firefly and *Renilla* luciferase activities were measured 18 hours after transfection by the Dual-Luciferase Reporter Assay System (Promega) using a Promega GloMax 20/20 luminometer. The relative firefly luciferase activities of the UTR constructs and pathway reporter constructs were analyzed.

Chemoresistance Profiling (IC50 Determination)

Clinical-grade (NCI Dictionary of Cancer Terms), pirarubicin (Pi, Wanle, Shenzhen) paclitaxel (Pa, Taiji, Sichuan), Adriamycin (Ad, Pfizer, Jiangsu), epirubicin hydrochloride (EH, Haizheng, Zhejiang), and cisplatin (Ci, Haosen, Jiangsu) were used. Relative $IC_{50}$ values were determined as previously described.

Apoptosis Analysis

Cells were harvested and rinsed with phosphate-buffered saline (PBS) twice. Then, 5 µl of fluorescein isothiocyanate (FITC)-labeled enhanced Annexin V and 5 µl (20 µg/ml) of propidium iodide were added to the 100 µl cell suspension. Following incubation in the dark for 15 min at room temperature, the samples were diluted with 400 µl PBS. Flow cytometry was carried out on a FACSCalibur instrument. The results were analyzed according to the manufacturer's instructions. The experiments were performed independently three times, and a representative result is shown herein.

RNA Analysis

Total RNA was isolated from the cells at the logarithmic phase using TRIzol reagent (Tiangen Biotech Co., Ltd., Beijing, China). For mRNA analysis, cDNA primed by oligo-dT was generated using a PrimeScript RT reagent kit (Tiangen Biotech Co., Ltd., Beijing, China), and the mRNA levels of the genes were quantified by duplex-qRT-PCR analysis using TaqMan probes with a different fluorescence for the β-actin (provided by Shing Gene, Shanghai, China) and a FTC-3000P PCR instrument (FUNGLYN BIOTECH INC, Canada). Using the $2^{-\Delta\Delta Ct}$ method, gene expression was normalized to β-actin and then compared between groups.

Bulge-Loop™ miRNA qRT-PCR

For detecting and quantifying the expression of specific miRNAs, RNA was reverse-transcribed using the Bulge-Loop™ miRNA qRT-PCR Primer Set (Ribobio) and quantified by SYBR Green-based real-time PCR analysis in a FTC-3000P (FUNGLYN BIOTECH INC, Canada). The Ct values of the target miRNAs were normalized to the Ct values of U6 RNA before quantification using the $2^{-\Delta\Delta Ct}$ method.

Western Blot

Cells were lysed with a lysis buffer (60 mM Tris-HCl, pH 6.8, 2% sodium dodecyl sulfate [SDS], 20% glycerol, 0.25% bromophenol blue, 1.25% 2-mercaptoethanol) and heated at 100° C. for 10 min before electrophoresis/Western blot analysis. The anti-ING5 antibody (10665-1-AP) was purchased from Proteintech, and anti-GAPDH antibody (AM1020a), anti-rabbit IgG peroxidase-conjugated antibody (LP1001b), and HRP-conjugated goat anti-mouse IgG antibody (LP1002a) were provided by Wuxiphama, Shanghai, China. The target bands were revealed by an enhanced chemiluminescence reaction (Pierce), and the relative density of each protein over GAPDH was quantified using a Gel-Pro Analyzer (Media Cybernetics).

In Vivo Studies

ING5 protein expression was measured using immunohistochemical analysis on 5-mm slices of formalin-fixed paraffin-embedded tumor xenografts in nude mice. To avoid inter-treatment bias, the tissue slides from all six groups were made on a single slide and subjected to the same immunostaining simultaneously. Antigens were retrieved by pretreating dewaxed sections in a microwave oven at 750 W for 5 min in a citrate buffer (pH 6) processed with the Super Sensitive Link-Labeled Detection System (Biogenex, Menarini, Florence, Italy). The enzymatic activities were developed using 3-amino-9-ethylcarbazole (Dako, Milan, Italy) as a chromogenic substrate. Following counterstaining with Mayer's hematoxylin (Invitrogen), slides were mounted in aqueous mounting medium (glycergel, Dako). Pictures were taken using a LEICA DM 4000B microscope, while the relative level of each protein was calculated using LEICA software. The percentage of the mock-over the chemotherapeutic-treated tumors was calculated and plotted.

Statistical Analysis

Data are presented as the means, and error bars indicate the standard deviation (S.D.) or standard error (S.E.). All of the statistical analyses were performed using Excel (Microsoft, Redmond, Wash.) or Prism (GraphPad Software Inc., La Jolla, Calif.). The two-tailed Student's t-test, one-way analysis of variance or the Mann-Whitney U test was used to calculate statistical significance. A P-value of <0.05 was considered significant.

Results

ING5 is a Negative Regulator of Multi-Chemoresistance in BCa Cells

Among 9051 differentially expressed genes between a multi-chemosensitive (5637) and a resistant BCa cell line (H-bc) that were revealed by an RNA-seq-based omic study, ING5 was among the top 10% most differentially expressed. The BCa chemoresistance-associated expression of the ING5 gene was confirmed by qRT-PCR analysis at the steady state mRNA level and a Western blot analysis at the protein level. The results showed that the ING5 protein (1.00:0.61) and mRNA expression levels were higher (RNA-seq-based omic: 1.00:0.28, and qRT-PCR analysis: 1.00:0.72,) in 5637 cells than in H-bc cells.

To demonstrate its potential role in BCa chemoresistance, this example suppressed ING5 mRNA expression to 33%, 47% and 21% of the NC control in 5637 cells by transfection of si-ING5-1, -2 and -3, respectively. The levels of drug-triggered cell death in the transfected cells at the $IC_{50}$ of various drugs (paclitaxel, Pa; Adriamycin, Ad; cisplatin, Ci; pirarubicin, Pi; epirubicin hydrochloride, EH) was then determined. The most effective siRNA (si-ING5-1) relieved cell death in the 5637 cells stressed by all five drugs except Pa. The $2^{nd}$ most effective siRNA (si-ING5-3) failed to desensitize 5637 cells to the cell-killing effects of Pa and Ci, while the least effective siRNA (si-ING5-2) was only able to reduce cell death in the EH-treated 5637 cells. These observations suggest that ING5's effect on the drug type-specific chemoresistance of 5637 cells is sensitive to the expression of the ING5 gene within the cell. This example further showed that forced upregulation of GFP-tagged ING5 protein (by Western blot analysis, and immunofluorescence analysis) desensitized the transfected H-bc cells to the cell death triggered by all five drugs. In conclusion, ING5 had a significant effect on drug-triggered cell death for four (Ad, Ci, Pi and EH) of the five drugs tested in BCa cells.

ING5 is a Direct Target of miR-193a-3p in BCa Cells

The critical role of microRNA (miR) genes in the multi-chemoresistance of cancer has been established. The DNA methylation-regulated miR-193a-3p confers 5-FU resistance to hepatocellular carcinoma (HCC) by repressing SRSF2 expression. MiR-193a-3p also promotes multi-chemoresistance in BCa cells by suppressing SRSF2, HIC2 PLAU, LOXL4, PSEN1 and HOXC9 and altering the activities of five signaling pathways: DNA damage, Notch, NF-κB, Myc/Max and oxidative stress. The miR-193a-3p level is significantly lower in 5637 than in H-bc cells, while its target genes SRSF2, HIC2 and PLAU are lower in H-bc than in 5637 cells, a pattern also displayed by ING5 in this pair of cell lines.

Incidentally, ING5 was on the list of miR-193a-3p targets suggested by TargetScan software. Therefore, we determined the ING5 level in miR-193a-3p mimic-transfected 5637 and antagomiR-transfected H-bc versus NC (a scrambled-sequence control)-transfected cells. In parallel with changes in the miR-193a-3p level, miR-193a-3p mimic transfection suppressed ING5 mRNA expression to nearly 76% and protein expression to 25% of the NC level in 5637 cells. Transfection with the miR-193a-3p antagomiR raised the ING5 mRNA level to 141% and the protein level to 145% of the level in the NC-transfected H-bc cells.

Next, we inserted the ING5 UTR (1-1037 bp) with either a wild-type or mutant miR-193-3p target sequence downstream of the firefly luciferase gene into the pGL3-control vector (Promega) to create the pGL3-ING5 UTR WT or the pGL3-ING5 UTR Mut construct, respectively. The pGL3-ING5 UTR WT, pGL3-ING5 UTR Mut and pGL3 constructs were individually transfected into 5637 and H-bc cells. The firefly luciferase activity was measured to determine whether the differentially expressed miR-193a-3p in this pair of cell lines was functional. As shown in, pGL3-ING5-UTR WT but not the other 2 reporter constructs produced significantly higher luciferase activity in 5637 than in H-bc cells. Furthermore, only the luciferase activity of pGL3-ING5-UTR WT was suppressed in the mimic-transfected 5637 cells and upregulated in the antagomiR-transfected H-bc cells relative to the pGL3 control. In conclusion, the ING5 gene is a direct post-transcriptional target of miR-193-3p.

We further compared the levels of drug-triggered cell death in 5637 cells transfected with miR-193a-3p mimic versus ING5 siRNAs. Whereas miR-193a-3p reduced the ING5 level to 40%, all three si-RNAs reduced the ING5 protein level to no more than 30% of the NC control and had no suppressive effects on the LOXL4 protein, another direct target of miR-193a-3p. The ING5 mRNA level was also reduced by miR-193a-3p and the siRNAs to comparable degrees. Although the miR-193a-3p mimic had a relatively weaker repressive effect on ING5, the mimic-transfected 5637 cells suffered less drug-triggered death in response to all five $IC_{50}$-dosed drugs, while only the most potent siRNA (si-ING5-1) significantly (but to a reduced extent in the cells stressed by Ad, Ci or Pi) decreased the level of cell death in 5637 cells stressed by Ad, Ci, Pi or EH, but not Pa. The observed disparity between the miR-193a-3p mimic and the most effective siRNA against ING5 (si-ING5-1) in terms of drug-triggered cell death is likely attributable to the down-regulation of other miR-193a-3p target proteins, such as SRSF2, PLAU, HIC2 and LOXL4 in mimic-transfected but not in si-ING5-1-transfected 5637 cells. Incidentally, the siRNA (-1, -2 and -3, respectively)-mediated ING5 repression reduced the percentage of late-apoptotic (and necrotic) cells from 11.4% to 4.33%, 4.90%, and 4.62% and decreased the percentage of early-stage apoptotic cells (the right lower quadrant) from 2.96% to 1.23%, 1.20% and 1.89%. Intriguingly, although miR-193a-3p mimic had the strongest resistance-promoting effect, it had a lower anti-apoptotic effect than the ING5 siRNAs, implying that other mechanisms, including G2 arrest, may be involved. Indeed, earlier examples have shown that miR-193a-3p mimic causes G2 arrest in 5637 cells, an effect that was not observed in ING5 siRNA-transfected 5637 cells. In the reverse experiment, the miR-193a-3p antagomiR sensitized the H-bc cells to the cytotoxicity caused by all five drugs, as did the GFP-ING5 expression constructs, to an even greater extent.

All of these observations suggest that ING5 acts as the downstream target of miR-193a-3p, mediating a significant part of miR-193a-3p's effect on BCa chemoresistance to Ad, Ci, Pi and EH in 5637 cells or to all five drugs in H-bc cells.
ING5 Positively Regulates the DNA Damage Response Pathway in the Context of BCa Multi-Chemoresistance Earlier examples show that miR-193a-3p regulates multi-chemoresistance by repressing the expression of three of its downstream targets (SRSF2, PLAU, HIC2, LOXL4, PSEN1 and HOXC9) and in turn altering the activities of five signaling pathways: DNA damage response, Notch, NF-κB, Myc/Max and oxidative stress. It is desirable to determine which of these five pathways are also affected by the forced changes in the ING5 level in both 5637 and H-bc cells. In parallel with the reduced ING5 levels, the activities of the DNA damage response, NF-κB and Myc/Max pathways were repressed by the ING5 siRNAs in a similar fashion to miR-193a-3p mimic, but they differed in potency. For example, the activity of the DNA damage response pathway was reduced by ING5 siRNAs-1, -2 and -3 to 43%, 64% and 48% of the NC level, respectively, but miR-193a-3p mimic reduced the activity to 17% of the NC level. We further assessed the changes in the mRNA levels of several genes in 5637 cells transfected with siRNA compared with the NC- and miR-193a-3p mimic-transfected cells, including the downstream gene targets of the DNA damage response pathway (CDKN1A and EDN1) NF-κB (RelA) pathway, and Myc/Max pathway (TERT and ODC1) as well as ING5. In parallel with the reduced ING5 mRNA expression levels, both the CDKN1A and ODC1 mRNA levels were down-regulated. Therefore, the ING5 connection to miR-193a-3p in 5637 cells in the context of BCa multi-chemoresistance is most likely attributable to its effect on the activities of these three pathways that are regulated by miR-193a-3p.

Last in this line of experiments, we transfected H-bc cells with a GFP-ING5 expression construct or a GFP (negative control) construct to overexpress ING5. Only the activity of the DNA damage response pathway among the pathways examined in 5637 cells was activated dramatically by both miR-193a-3p antagomiR and EGP-ING5 overexpression. Therefore, ING5's role in mediating miR-193a-3p's effect on BCa chemoresistance is principally accomplished by its impact on the DNA damage response pathway.
ING5 Expression is Reduced in miR-193a-3p agomiR-Injected 5637 Tumor Xenografts and Increased in antago-miR-Injected H-Bc Tumor Xenografts in Nude Mice In our previous study, we showed that miR-193a-3p promotes Pa chemoresistance in BCa cells in tumor xenografts of nude mice by repressing three of its targets in the tumor tissues: SRSF2, PLAU and HIC2. In the present study, we semi-quantified the ING5 levels in the same set of the xenografts by immunohistological analysis. The injection of either miR-193a-3p agomiR into 5637 tumor xenografts or of the antagomiR into H-bc tumor xenografts indeed led the opposite changes of ING5 protein overexpression in the tumor tissues. This observation further strengthens the notion that ING5 has a role in miR-193a-3p's effect promoting Pa-chemoresistance in BCa cells.

In summary, this example shows that the ING5 gene, together with other downstream genes (SRSF2, PLAU and HIC2), mediates a significant part of miR-193a-3p's positive impact on multi-chemoresistance in BCa cells, mainly via its positive impact on the DNA damage response pathway.

Example 6. The Methylation Status and Expression Level of miR-193a-3p Correlate with Bladder Cancer Cells' Resistance to Certain Drugs This example examines the methylation status of the miR-193a gene and the expression level of the miR-193a-3p transcript across nine different bladder cancer cell lines (5637, SCaBER, Biu87, T24, SV-HUC-1, J-82, EJ, H-bc, UM-UC-3, and SV-HUC-1) each of which has different sensitivity to eight chemotherapeutic drugs.

As shown in Table 1 below, the methylation status and the expression level of miR-193a-3p correlate with five out of the eight drugs. That is, the miR-193a gene was methylated and lowly expressed in cells sensitive to the drugs and not methylated and highly expressed in cells resistant to the drugs.

TABLE 1

Correlation between miR-193a-3p status and drug resistance

| Drug | Short Name | Correlation |
|---|---|---|
| Pirarubicin | Pi | Yes |
| Pacilitaxol | Pa | Yes |
| Adriamycin | Ad | Yes |
| Epirubicin hydrochloride | EH | Yes |
| Cisplatin | Ci | Yes |

TABLE 1-continued

Correlation between miR-193a-3p status and drug resistance

| Drug | Short Name | Correlation |
|---|---|---|
| Hydroxycamptothecin | Hy | No |
| Gemcitabine | Ge | No |
| Mitomycin | Mi | No |

Figure 2:
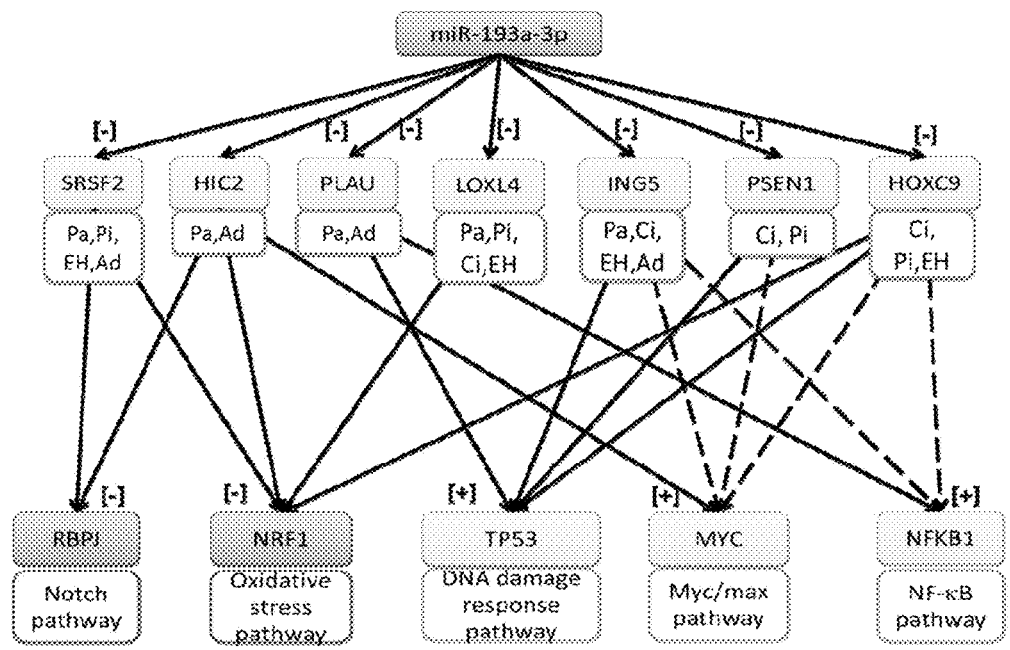
FIG. 2 shows that each of the seven target genes is associated with one or more biological pathways relating to drug resistance, and the combination of the status of miR-193a-3p and the status of each of the genes exhibited synergism in correlating to resistance to the indicated drugs.

The example then examined whether the combination of the status of miR-193-3p with the expression level (RNA or protein) of each of the seven genes that miR-193-3p regulates lead to better correlation with the treatment outcomes. Such combinations, as FIGS. 1 and 2 show, exhibited synergism in correlating with the treatment outcome of one or more of the five drugs (FIG. 2). These results are also summarized in Table 2.

TABLE 2

Correlation between miR-193a-3p/downstream gene status and drug resistance

| Drug | Correlation with miR-193a-3p + |
|---|---|
| Pi | SRSF2, LOXL4, PSEN1, HOXC9 |
| Pa | SRSF2, HIC2, PLAU, LOXL4, ING5 |
| Ad | SRSF2, HIC2, PLAU, ING5 |
| EH | SRSF2, LOXL4, ING5, HOXC9 |
| Ci | LOXL4, ING5, PSEN1, HOXC9 |

The disclosure illustratively described herein may suitably be practiced in the absence of any element or elements, limitation or limitations, not specifically disclosed herein. Thus, for example, the terms "comprising", "including", containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

Thus, it should be understood that although the present disclosure has been specifically disclosed by preferred embodiments and optional features, modification, improvement and variation of the disclosure embodied therein herein disclosed may be resorted to by those skilled in the art, and that such modifications, improvements and variations are considered to be within the scope of this disclosure. The materials, methods, and examples provided here are representative of preferred embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

The invention claimed is:

1. A method of treating a human bladder cancer patient, comprising:
    measuring, in a sample that comprises tumor DNA of the patient, the methylation status of one or more CpG sites associated with the miR-193a gene,
    identifying the patient as sensitive to a chemotherapeutic agent selected from the group consisting of pirarubicin, paclitaxel, adriamycin, epirubicin hydrochloride, and cisplatin if the CpG sites are methylated, and
    administering to the patient the chemotherapeutic agent.

2. The method of claim 1, wherein the sample is a urine sediment sample.

3. The method of claim 1, wherein the sample comprises a tumor cell.

4. The method of claim 3, further comprising measuring the expression level of a target gene selected from SRSF2, PLAU, HIC2, LOXL4, HOXC9, PSEN1 and ING5 in the tumor cell, and determining that the bladder cancer patient is suitable for the therapy if the CpG sites are methylated and the expression level of the target gene is increased as compared to a control bladder cancer patient that is resistant to the therapy.

5. A method for identifying a suitable chemotherapeutic drug for and treating a human bladder cancer patient, comprising:
    measuring, in a sample that comprises a tumor cell of the patient, (a) the methylation status of one or more CpG sites associated with the miR-193a gene or the expression level of the miR-193a-3p RNA and (b) the expression level of a target gene selected from SRSF2, PLAU, HIC2, LOXL4, HOXC9, PSEN1 and ING5,
    identifying the patient as suitable for therapy with:
        (i) pirarubicin, if (a) the CpG sites are methylated or the expression level of the miR-193a-3p RNA is decreased as compared to a control bladder cancer patient that is resistant to pirarubicin and (b) the expression level of any one of SRSF2, LOXL4, PSEN1 and HOXC9 is increased as compared to a control bladder cancer patient that is resistant to pirarubicin;
        (ii) paclitaxel, if (a) the CpG sites are methylated or the expression level of the miR-193a-3p RNA is decreased as compared to a control bladder cancer patient that is resistant to paclitaxel and (b) the expression level of any one of SRSF2, HIC2, PLAU, LOXL4 and ING5 is increased as compared to a control bladder cancer patient that is resistant to paclitaxel;
        (iii) adriamycin, if (a) the CpG sites are methylated or the expression level of the miR-193a-3p RNA is decreased as compared to a control bladder cancer patient that is resistant to adriamycin and (b) the expression level of any one of SRSF2, HIC2, PLAU and ING5 is increased as compared to a control bladder cancer patient that is resistant to adriamycin;
        (iv) epirubicin hydrochloride, if (a) the CpG sites are methylated or the expression level of the miR-193a-3p RNA is decreased as compared to a control bladder cancer patient that is resistant to epirubicin hydrochloride and (b) the expression level of any one of SRSF2, LOXL4, ING5 and HOXC9 is increased as compared to a control bladder cancer patient that is resistant to epirubicin hydrochloride; or (v) cisplatin, if (a) the CpG sites are methylated or the expression level of the miR-193a-3p RNA is decreased as compared to a control bladder cancer patient that is resistant to cisplatin and (b) the expression level of any one of LOXL4, ING5, PSEN1 and HOXC9 is increased as compared to a control bladder cancer patient that is resistant to cisplatin, and administering to the patient the identified suitable therapy.

6. The method of claim 5, wherein the sample is a tumor tissue or tumor cell.

* * * * *